(12) United States Patent
Daftary et al.

(10) Patent No.: US 9,883,925 B2
(45) Date of Patent: Feb. 6, 2018

(54) RESTORATION DENTAL IMPLANT AND METHOD

(71) Applicants: Fereidoun Daftary, Beverly Hills, CA (US); Oded Bahat, Beverly Hills, CA (US)

(72) Inventors: Fereidoun Daftary, Beverly Hills, CA (US); Oded Bahat, Beverly Hills, CA (US)

(*) Notice: Subject to any disclaimer, the term of this patent is extended or adjusted under 35 U.S.C. 154(b) by 35 days.

(21) Appl. No.: 14/953,358

(22) Filed: Nov. 29, 2015

(65) Prior Publication Data

US 2016/0151129 A1 Jun. 2, 2016

Related U.S. Application Data

(63) Continuation of application No. 14/583,392, filed on Dec. 26, 2014.

(60) Provisional application No. 62/085,514, filed on Nov. 29, 2014, provisional application No. 62/131,754, filed on Mar. 11, 2015.

(51) Int. Cl.
*A61C 8/00* (2006.01)
*A61C 8/02* (2006.01)

(52) U.S. Cl.
CPC .......... *A61C 8/0037* (2013.01); *A61C 8/0006* (2013.01); *A61C 8/0018* (2013.01); *A61C 8/0025* (2013.01); *A61C 8/0054* (2013.01); *A61C 8/0066* (2013.01); *A61C 8/0068* (2013.01); *A61C 8/0069* (2013.01); *A61C 8/0077* (2013.01); *A61C 8/0089* (2013.01)

(58) Field of Classification Search
CPC ....... A61C 8/005; A61C 8/006; A61C 8/0018; A61C 8/0054; A61C 8/0069; A61C 8/0077
USPC .................................................. 433/173–176
See application file for complete search history.

(56) References Cited

U.S. PATENT DOCUMENTS

| | | | | |
|---|---|---|---|---|
| 5,785,525 A * | 7/1998 | Weissman | ............ | A61C 8/0018 433/174 |
| 6,039,568 A * | 3/2000 | Hinds | .................. | A61C 8/0036 433/173 |
| 7,179,088 B2 * | 2/2007 | Schulter | ............... | A61C 8/0018 433/173 |
| 7,341,453 B2 * | 3/2008 | Coatoam | ................ | A61C 8/005 433/173 |
| 8,221,119 B1 * | 7/2012 | Valen | ................... | A61C 8/0025 433/174 |
| 8,449,297 B2 * | 5/2013 | Boehm-Van Diggelen | | A61C 8/001 433/173 |
| 2009/0280454 A1 * | 11/2009 | Hanna | .................. | A61C 8/0018 433/174 |
| 2014/0242546 A1 * | 8/2014 | Babiner | ............... | A61C 8/0069 433/174 |

* cited by examiner

*Primary Examiner* — Cris L Rodriguez
*Assistant Examiner* — Matthew Saunders
(74) *Attorney, Agent, or Firm* — Thomas I. Rozsa

(57) ABSTRACT

An implant fixture is disclosed. The implant fixture contains an elongated shaft section, and a head section, wherein the head section contains at least one concave area for bone growth therein.

17 Claims, 18 Drawing Sheets

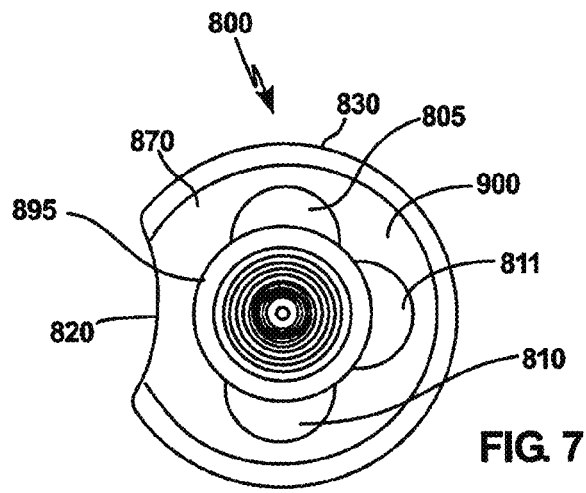
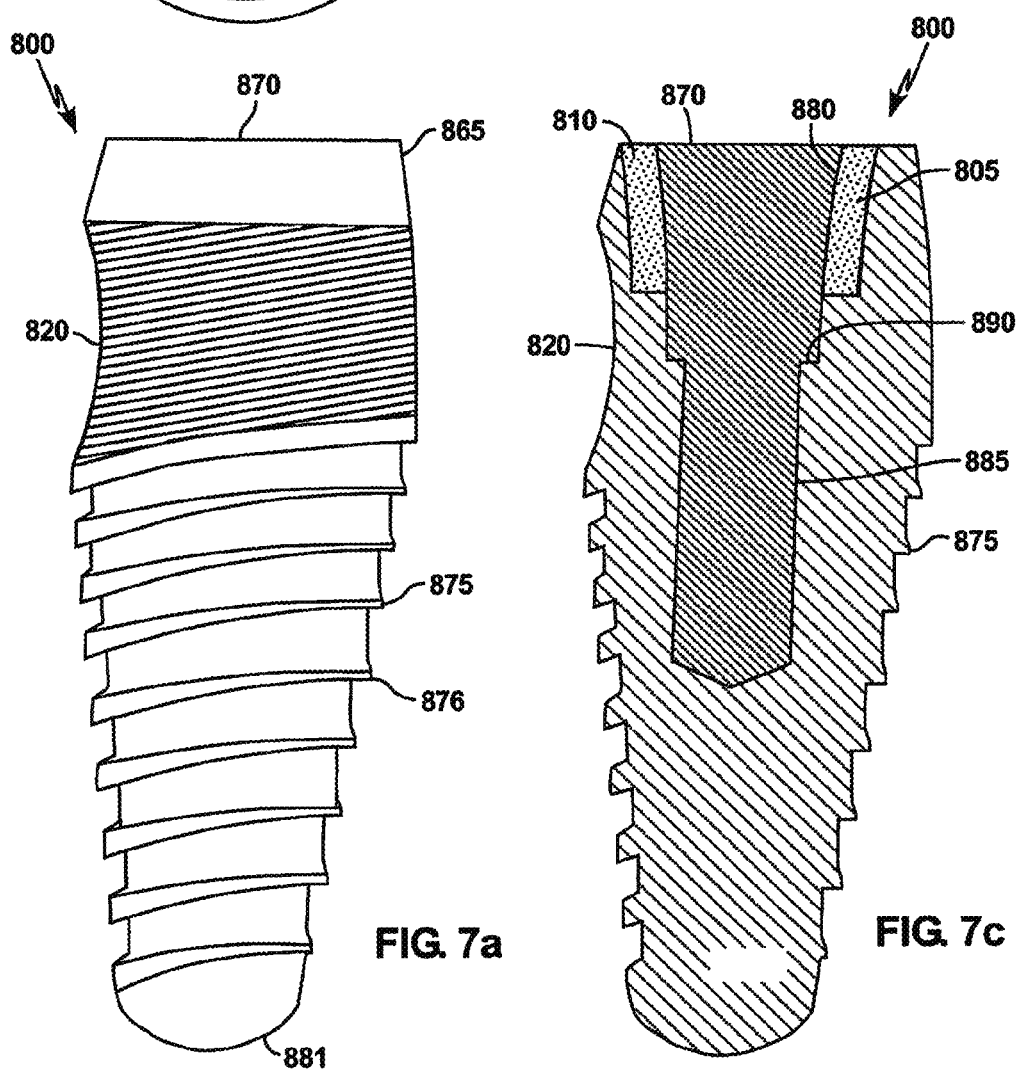
FIG. 7b
FIG. 7a
FIG. 7c

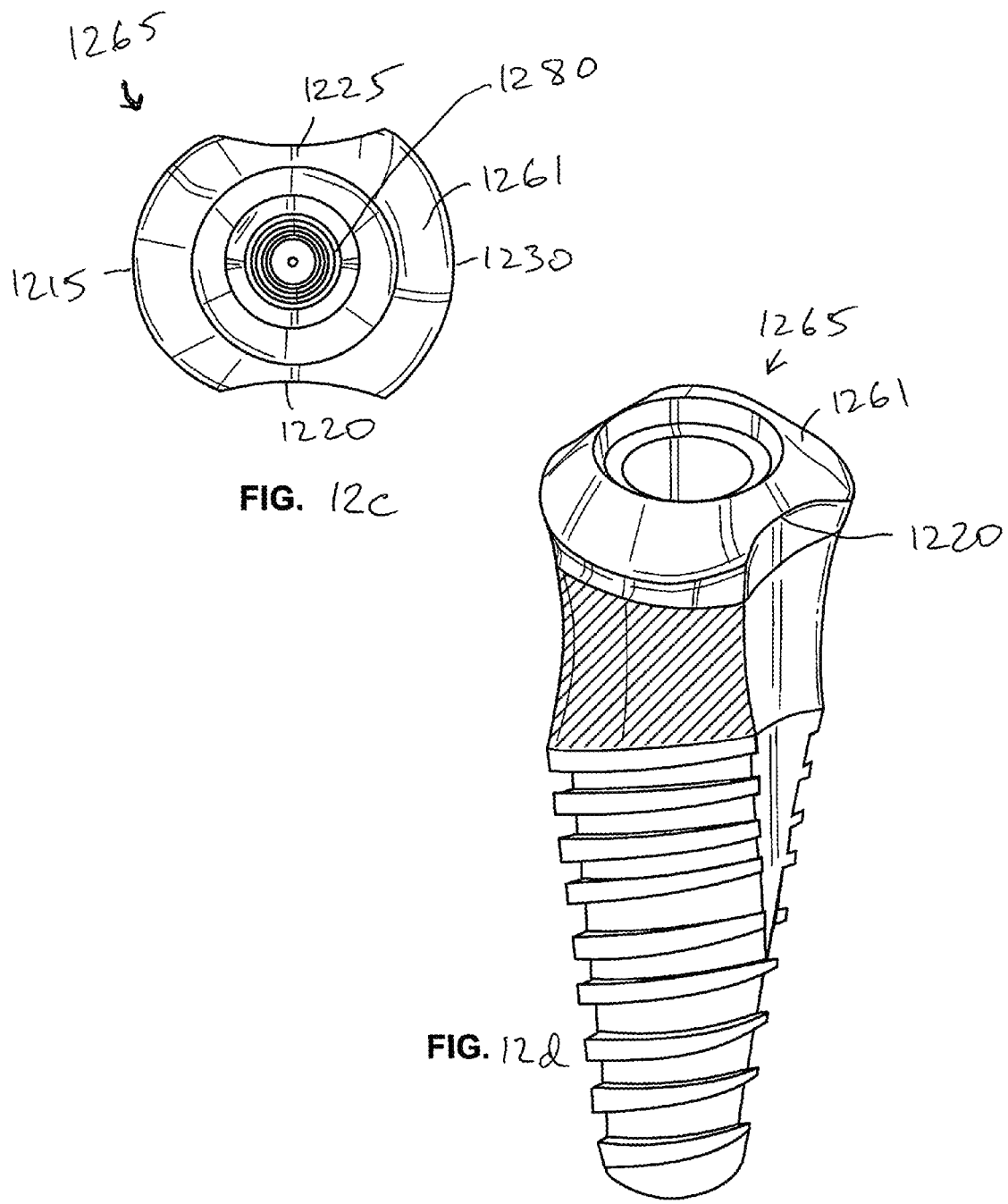

RESTORATION DENTAL IMPLANT AND METHOD

CROSS REFERENCE TO RELATED APPLICATIONS

This application claims the benefit of U.S. Provisional Application No. 62/131,754, filed on Mar. 11, 2015, which is incorporated herein by reference in its entirety. This application claims the benefit of U.S. Provisional Application No. 62/085,514, filed on Nov. 29, 2014, which is incorporated herein by reference in its entirety. This application claims the benefit of U.S. application Ser. No. 14/583,392, filed on Dec. 26, 2014, which is incorporated herein by reference in its entirety.

FIELD

The present invention relates to the filed of dental implants.

BACKGROUND

Restorations supported by dental implants with adjacent and/or opposing teeth have been performed by thousands of clinicians. An exemplary restoration process is shown in FIGS. 1a-d. Referring to FIG. 1a, an alveolus 10 is formed in a patient's jawbone 15 to accommodate a dental implant fixture 20. Once the dental implant fixture 20 is securely in the alveolus 10 (shown in FIG. 1b), an abutment member 25 is coupled with the dental implant fixture 20 (shown FIGS. 1c-d). The restoration process is completed after tooth analogue 30 is coupled with the abutment member 25.

In view of the recent research, it has been determined that some people with single-tooth and/or multiple-tooth implant restorations exhibit esthetic, functional, restorative and/or periodontal ramifications of subtle continued craniofacial growth that occurs after the implant restorations are performed.

Craniofacial growth may influence the relationship of implant restorations to the remaining teeth and jaw structure by, for example, causing changes in occlusion, causing migration of teeth with subsequent effect of opening contact, and/or causing changes to anterior esthetic.

Changes in occlusion can be due to continued growth in the arch containing the implants, as well as the opposing arch. In both situations, the position of the implants and associated restoration are static whereas the teeth are subject to movement in both facial and occlusal directions. These potential changes are not gender-specific. For situations such as posterior free-end implant restorations supporting significant occlusal loads, these movements can negate the effectiveness of the implant restoration over time, placing unfavorable stresses on the remaining dentition.

When natural teeth are present in the same arch with dental implants, an unforeseen long-term complication observed by many has been the opening of contacts between the implant restoration and typically the natural tooth anterior to the implant restoration. With loss of the natural tooth contact mesial to the implant restoration significantly affected by age and condition of the opposing dentition.

Besides functional changes and consequences in occlusion and opening of contacts, it has been observed that subtle growth over time also can change esthetic results once thought to be stable. Discrepancies have become manifest in three visible areas relative to adjacent teeth: the incisal edge length, the gingival margin height, and the facial contour alignment. Extrusion and up righting of the anterior teeth can simultaneously cause all three discrepancies. Thinning of labial soft/hard tissue over the implant or abutment can be a further consequence accompanying this subtle growth process.

A discrepancy in facial alignment making the anterior implant restoration relatively more labial may or may not be able to be suitability modified or revised, depending not only on the severity of the occurrence but also on such factors as implant axial alignment, available soft-tissue depth, and labial/palatal positioning of the implant in the ridge. A progressive discrepancy between the implant restoration's cervical gingival margin and that of the adjacent natural teeth may be an esthetic complication with no easy resolution.

In view of the above, a need exists for an improved dental implant.

BRIEF DESCRIPTION OF THE FIGURES

FIG. 7a depicts the dental implant fixture according to some embodiments of the present disclosure.
FIG. 7b depicts a top plan view of the dental implant shown in FIG. 7a.
FIG. 7c depicts a cross-sectional view of the dental implant fixture shown in FIG. 7a.
FIG. 12a-d depict another dental implant system according to some embodiments of the present disclosure.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

According to one aspect, an implant fixture implantable in an alveolus of a patient's jawbone is presently disclosed. The implant fixture comprises an elongated shaft section, and a head section comprising at least one narrower side surface area, wherein the narrow side surface area provides an area for bone growth therein to compensate for jawbone deterioration adjacent to the implant fixture due to craniofacial growth According to another aspect, an implant fixture implantable in an alveolus of a patient's jawbone is presently disclosed. The implant fixture comprises an elongated shaft section, and a head section, wherein the head section comprises at least one concave area for bone growth therein.

According to another aspect, an implant fixture implantable in an alveolus of a patient's jawbone is presently disclosed. The implant fixture comprises an elongated shaft section with a distal end, and a head section with a proximal end, wherein the head section comprises a first diameter adjacent to the elongated shaft section and a second diameter adjacent to the proximal end, wherein the elongated shaft section comprises a first diameter adjacent to the head section and a second diameter adjacent to the distal end, wherein the second diameter of the head section is less than the first diameter of the elongated shaft section.

Figures 1A, 1B, 1C, 1D:
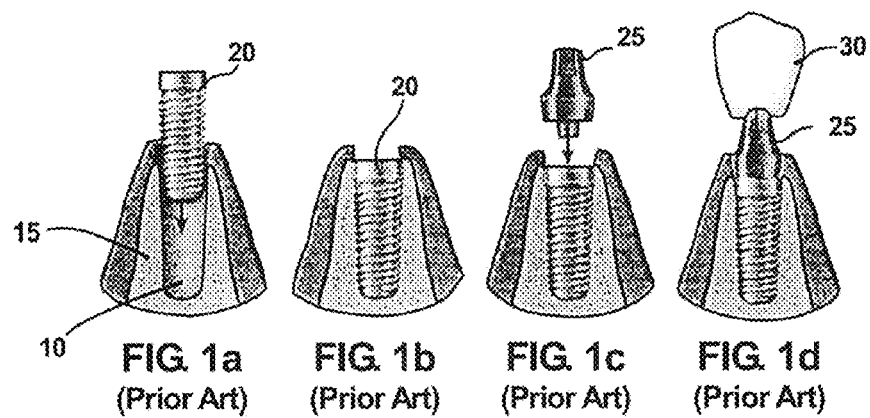
FIGS. 1a-d depict restoration process known in the art.
Figure 2A:
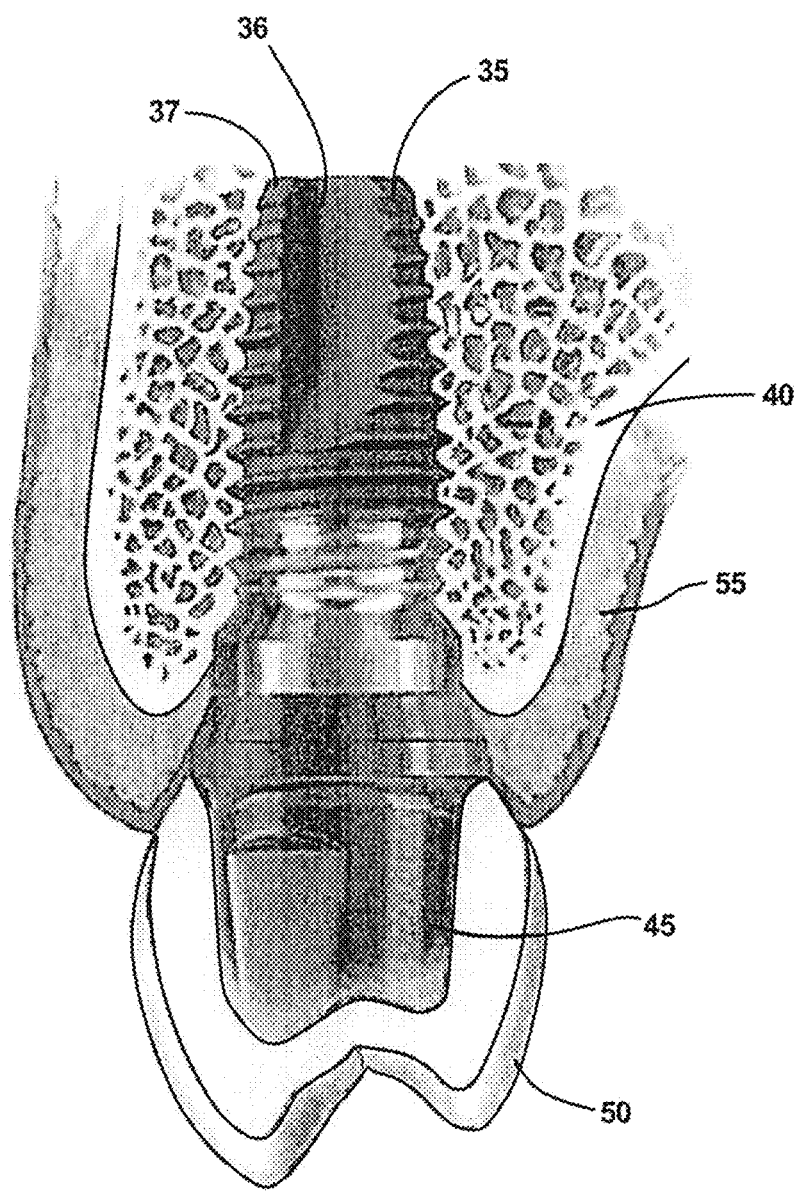
FIGS. 2a-b depict dental implant known in the art.

FIG. 2a depicts a dental implant fixture 35 as known in the art embedded within an alveolus formed in a jawbone 40 and coupled with an abutment member 45 and tooth analogue 50. The dental implant fixture 35 comprises a longitudinal groove (i.e. back cut) 36 extending from the narrow distal end 37 towards the abutment member 45. The longitudinal groove 36 provides a greater surface area into which bone growth are formed to prevent the implant fixture 35 from vertical and rotational movements within the jawbone 40.

Figure 2B:
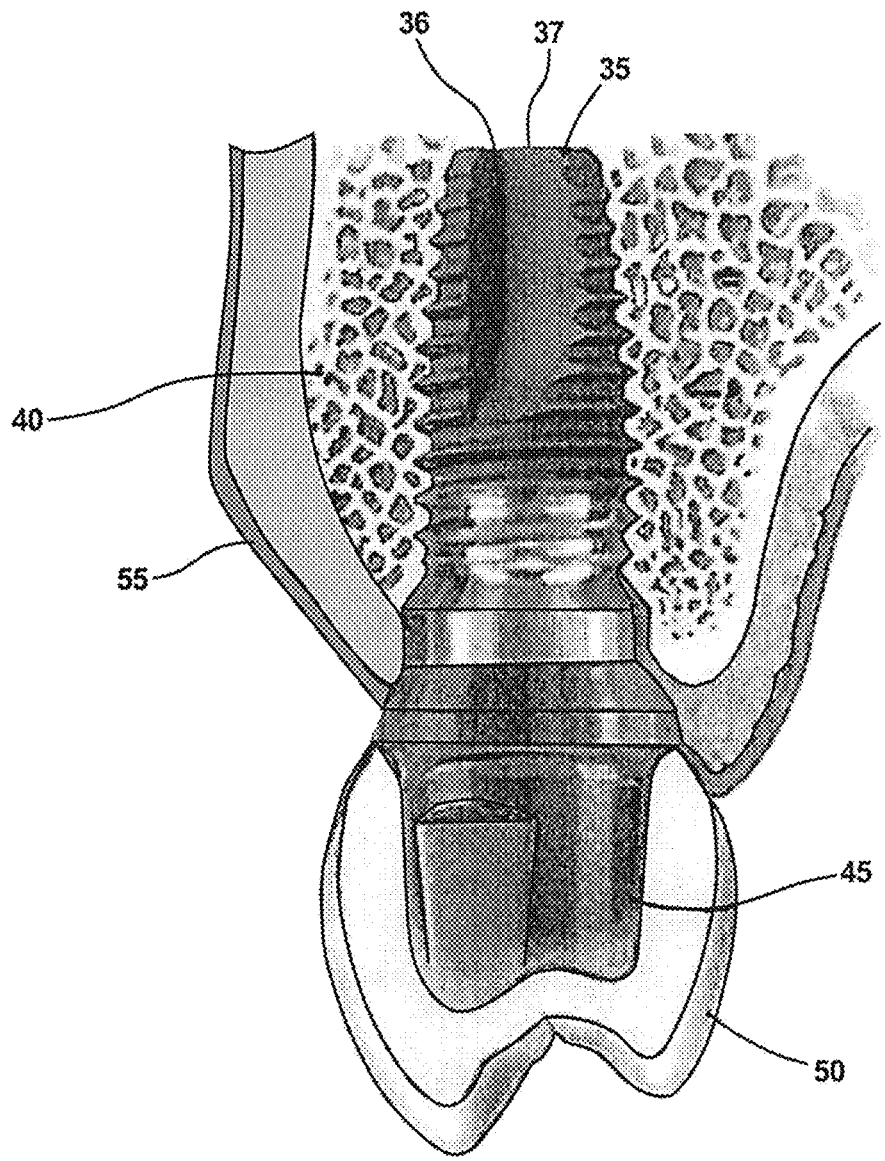

Due to craniofacial growth, over time, the jawbone 40 and/or soft tissue 55 may at least partially deteriorate adjacent to the dental implant fixture 35 to expose the dental implant fixture 35 and/or the abutment member 45 as shown in FIG. 2b. When this occurs, the dental implant fixture 35 is removed using processes known in the art. The process of removing the dental implant fixture 35 is complex at least in part due to the bone growth within the longitudinal groove 36 which prevent the dental implant fixture 35 from being unscrewed from the jawbone 40.

Figure 3A:
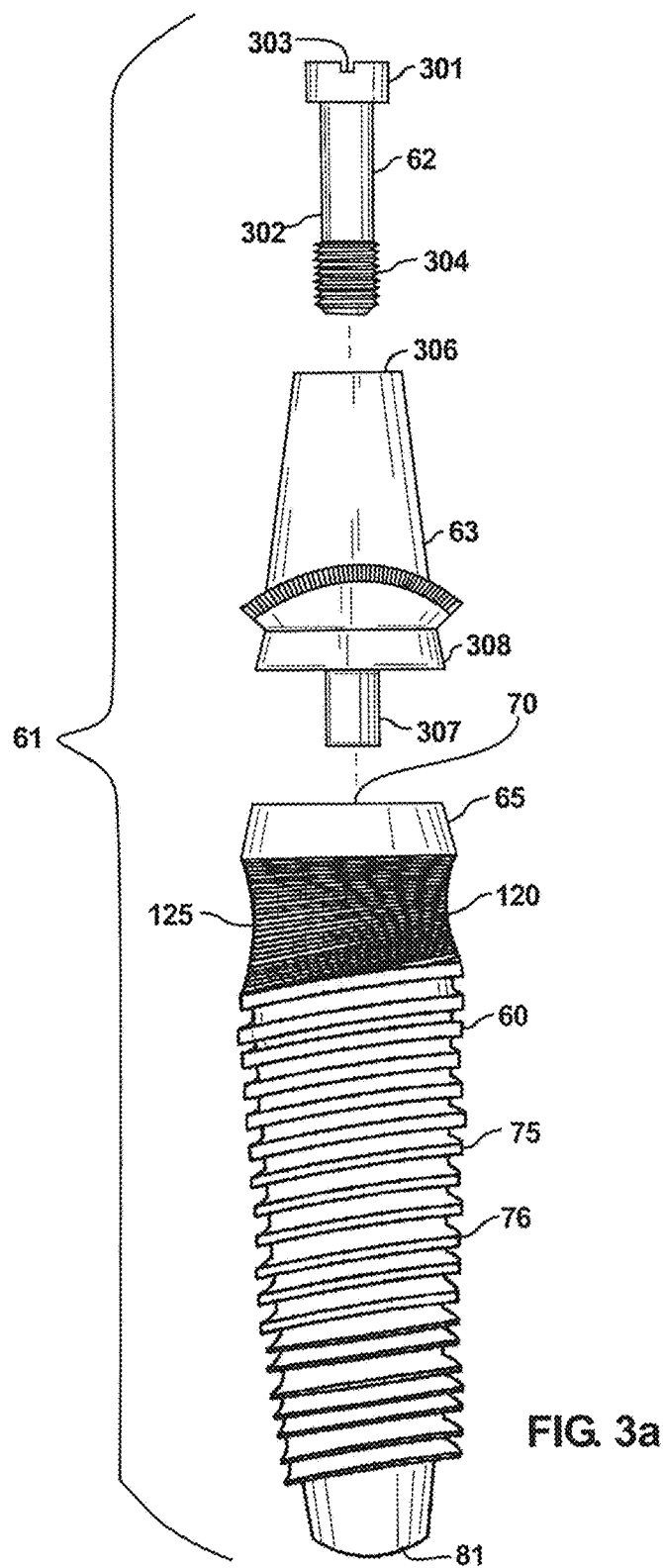
FIG. 3a depicts a dental implant system according to some embodiments of the present disclosure.

Referring to FIG. 3a, a dental implant system 61 is shown according to the present disclosure. In some embodiments, the dental implant system 61 comprises a bolt member 62, an abutment member 63, and a dental implant fixture 60.

In some embodiments, the bolt member 62 comprises a head segment 301 and a shaft segment 302. In some embodiments, the head segment 301 is generally disc shaped with a top notch or cross notch 303 or any other suitable means to accommodate a driving tool, for example, a screwdriver or any other tool for rotating the bolt member 62. In some embodiments, the shaft segment 302 has one end coupled with the head segment 301. In some embodiments, the shaft segment 302 comprises an outer screw threads 304 which are located opposite from the head segment 301 and extend along at least a portion of its length.

Figure 3B:
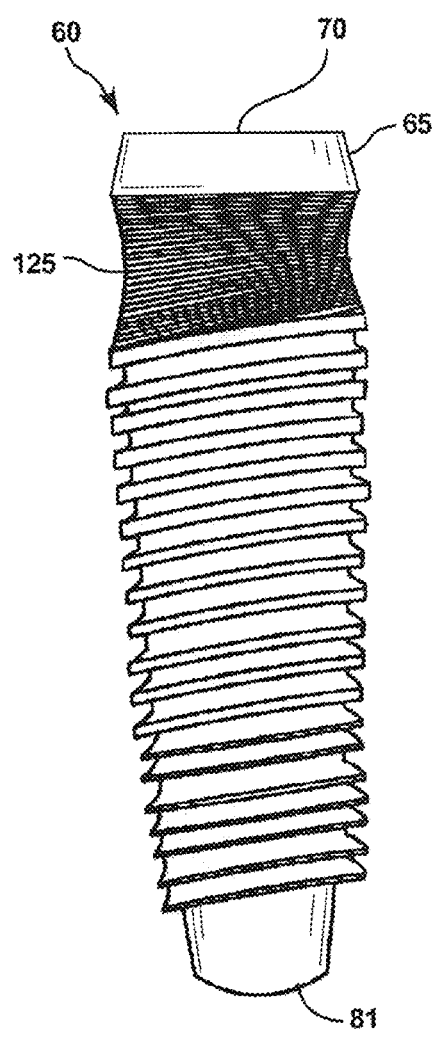
FIG. 3b depicts a dental implant fixture according to some embodiments of the present disclosure.

Referring to FIG. 3b, a dental implant fixture 60 is shown according to the present disclosure. In some embodiments presently disclosed, the dental implant fixture 60 comprises a head section 65 with a proximal end 70. In some embodiments, the fixture 60 comprises an elongated shaft section 75 with a distal end 81. In some embodiments, the head section 65 is integrally coupled with the shaft section 75 to form a one-piece implant fixture 60. This prevents bacteria or other infection growth between the head section and the shaft section of the implant fixture 60. In some embodiments, the elongated shaft section 75 is tapered.

Figure 4:
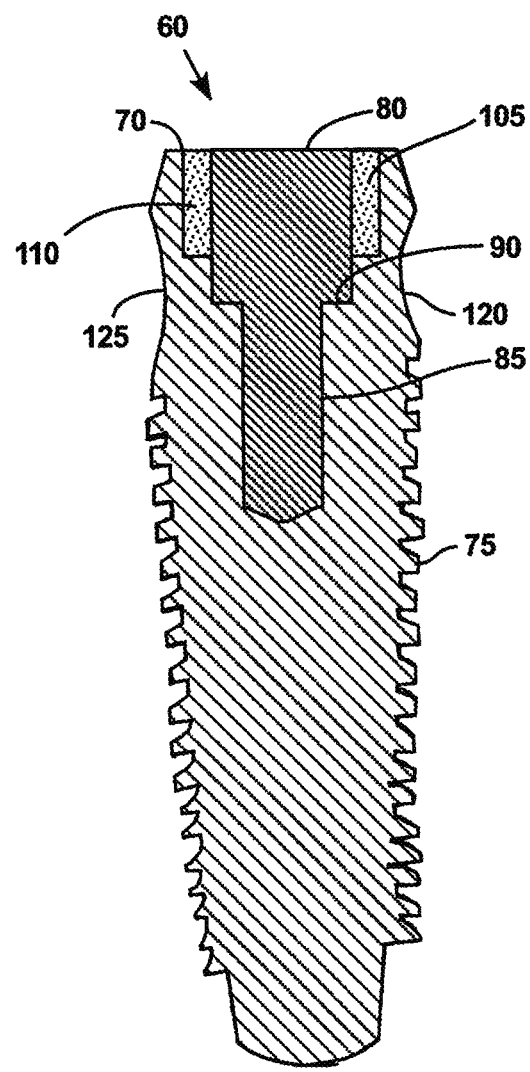
FIG. 4 depicts a cross-sectional view of the dental implant fixture shown in FIG. 3b.

In some embodiments, the implant fixture 60 comprises a stepped interior closed bore 80 extending partially downward from the proximal end 70 into the shaft section 75. In some embodiments, the stepped interior closed bore 80 is off-center. In some embodiments, the interior closed bore 80 comprises inner screw threads 85 along at least a portion of its length and an annular shelf 90 located above the inner screw threads 85 (as shown in FIG. 4). In some embodiment, the inner screw threads 85 are configured to accommodate the outer screw threads 304 of the bolt member 62. In some embodiments, the stepped interior closed bore 80 is configured to accommodate a protruding engagement end 307 (described in more detail below) of the abutment member 63.

Figure 5A:
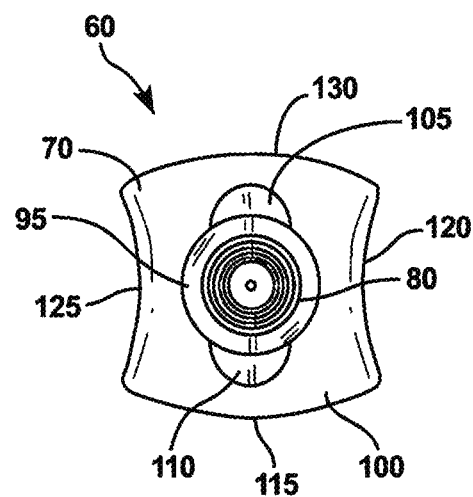
FIG. 5a depicts a top plan view of the dental implant fixture shown in FIG. 3b.

Referring to FIG. 5a, a top plan view of the implant fixture 60 is shown according to some embodiments presently disclosed. In some embodiments, the proximal end 70 has a circular flat surface 95 surrounded by a periphery surface 100 comprising a long-axis and a short axis. In some embodiments, the proximal end 70 further comprises two or more apertures 105, 110 for accommodating small tips of a standard dental tool, for example, implant mount or hand driver for orienting the implant fixture 60 and/or antirotational means for the abutment member 63. In some embodiments, the head section 65 comprises at least one narrower facial-side surface area 120 and at least one wider interproximal-side surface area 115. The facial-side surface area 120 accommodates the contour of the gingival tissue at the facial-side of the patient's oral cavity, which is located adjacent to the interior surface of the patient's lip, while the interproximal-side surface area 115 accommodates the contour of the gingival tissue at the interproximal-side of the patient's oral cavity which is located adjacent to the patient's other tooth and/or implant. In some embodiments, the facial-side surface area 120 is concaved toward the center of the circular flat surface 95.

In some embodiments, the head section 65 comprises a narrower lingual-side surface area 125 and at least one wider interproximal-side surface area 130. The lingual-side surface area 125 accommodates the contour of the gingival tissue at the lingual-side of the patient's oral cavity which is located adjacent to the patient's tongue or palate, while the interproximal-side surface area 130 accommodates the contour of the gingival tissue at the interproximal-side of the patient's oral cavity which is located adjacent to the patient's other tooth and/or implant. In some embodiments, the lingual-side surface area 125 is concaved toward the center of the circular flat surface 95.

In some embodiments, the facial-side surface area 120 and/or the lingual-side surface area 125 provide an area for bone growth therein to compensate for jawbone deterioration adjacent to the implant fixture 60 due to craniofacial growth. In some embodiments, the facial-side surface area 120 and/or the narrower lingual-side surface area 125 provide an arch shaped area for bone growth therein to compensate for jawbone deterioration adjacent to the implant fixture 60 due to craniofacial growth. In some embodiments, the facial-side surface area 120 and/or the narrower lingual-side surface area 125 provide a flat area for bone growth to compensate for jawbone deterioration adjacent to the implant fixture 60 due to craniofacial growth. In some embodiments, the facial-side surface area 120 and/or the narrower lingual-side surface area 125 provide a concave shaped area for bone growth therein to compensate for jawbone deterioration adjacent to the implant fixture 60 due to craniofacial growth. Increasing bone volume and/or soft tissue volume adjacent to the facial-side surface area 120 and/or the narrower lingual-side surface area 125 prevents early exposure of the implant fixture 60.

In some embodiments, the facial-side surface area 120 and/or the lingual-side surface area 125 provide a concave shaped area to improve bone formation due to the gap between the existing bone and the facial-side surface area 120 and/or the lingual-side surface area 125. In some embodiments, the facial-side surface area 120 and/or the lingual-side surface area 125 provide a concave shaped area to allow greater bone growth therein. In some embodiments, the facial-side surface area 120 and/or the lingual-side surface area 125 provide a concave shaped area to prevent/minimize pressure between the bone and the head section 65 during and/or immediately after the procedure. Preventing and/or minimizing pressure between the bone and the head section 65 during and/or immediately after the procedure prevent resorption of the bone around the head section 65 and/or allows increased bone formation around the head section 65. In some embodiments, the facial-side surface area 120 and/or the lingual-side surface area 125 provide a concave shaped area to allow bone and/or soft tissue growth therein.

In some embodiments, the dental implant fixture 60 does not comprise the longitudinal groove 36 (shown in FIGS. 2a-b) to prevent bone growth therein so as to allow the dental implant fixture 60 to be removed with less damage to patient's jawbone. In some embodiments, the facial-side surface area 120 and/or the lingual-side surface area 125 provide an area where bone growth can grow therein to prevent the implant fixture 60 from vertical and rotational movements within the patient's jawbone.

In some embodiments, the shaft section 75 comprises an outer screw thread 76 extending along at least a portion of its length. In some embodiments, the outer screw thread 76 is continuous. In some embodiments, the outer screw thread 76 is V-Thread, Square Thread, Buttress Thread, Reverse Buttress Thread or a combination of two or more of these threads. In some embodiments, the shaft section 75 comprises a substantially longitudinal groove or back cut (not shown) extending from the distal end 81 towards the head section 65. The longitudinal groove (not shown) provides a greater surface area into which bone growth is formed to prevent the implant fixture 60 from vertical and rotational movements within the jawbone.

Referring to FIG. 3a, in some embodiments, an abutment member 63 comprises a distal end 306 with a circular opening to accommodate the shaft segment 302 of the bolt member 62. Referring to FIG. 3a, in some embodiments, an abutment member 63 comprises a proximal portion 308 with a protruding engagement end 307 extending there from.

Figure 5B:
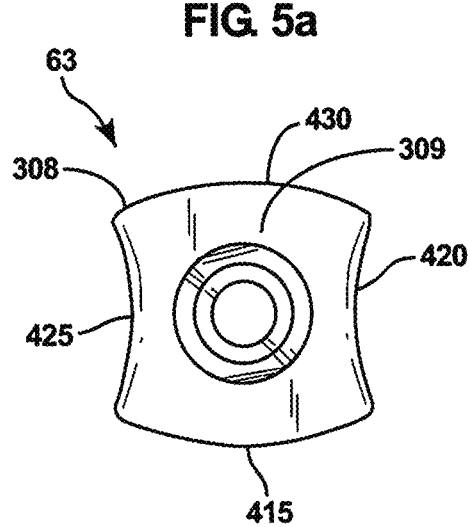
FIG. 5b depicts a bottom plan view of an abutment member according to some embodiments of the present disclosure.

Referring to FIG. 5b, a bottom plan view of the abutment member 63 is shown according to some embodiments presently disclosed. According to some embodiments, the proximal portion 308 comprises a surface 309. In some embodiments, the surface 309 comprises a long-axis and a short axis. In some embodiments, the proximal portion 308 comprises at least one narrower facial-side surface area 420 and at least one wider interproximal-side surface area 415. In some embodiments, the facial-side surface area 420 is substantially similar to the facial-side surface area 120. In some embodiments, the interproximal-side surface area 415 is substantially similar to the interproximal-side surface area 115. In some embodiments, the facial-side surface area 420 is concaved toward the center of the abutment member 63.

In some embodiments, the proximal portion 308 comprises a narrower lingual-side surface area 425 and at least one wider interproximal-side surface area 430. In some embodiments, the lingual-side surface area 425 is substantially similar to the lingual-side surface area 125. In some embodiments, the interproximal-side surface area 430 is substantially similar to the interproximal-side surface area 130. In some embodiments, the lingual-side surface area 425 is concaved toward the center of the abutment member 63.

Figure 3C:
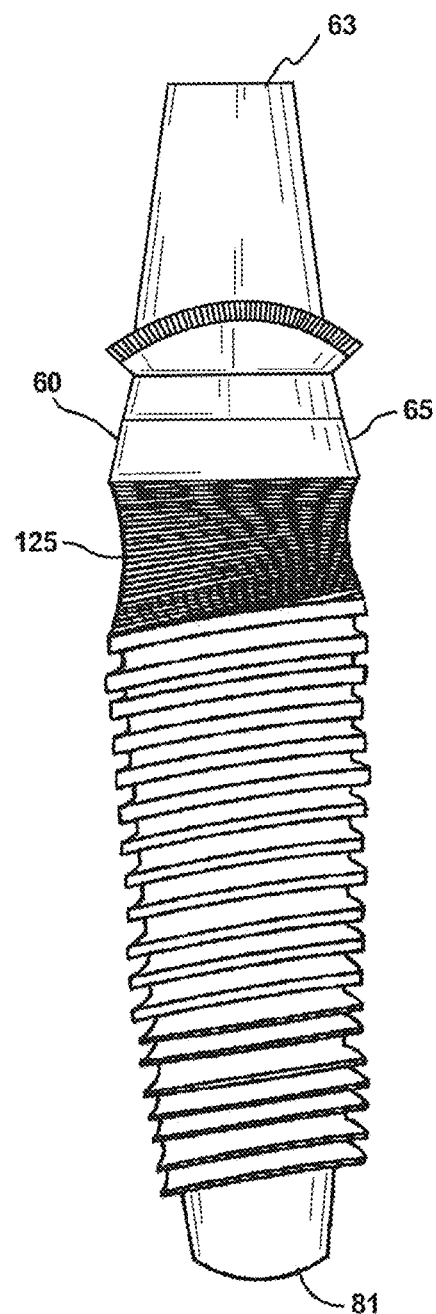
FIG. 3c depicts a dental implant fixture according to some embodiments of the present disclosure.

In some embodiment, an abutment member 63 is configured to couple with the head section 65 as shown in FIG. 3c. In some embodiment, an abutment member 63 is configured to couple with the head section 65 so as to align the facial-side surface area 420 with the facial-side surface area 120. In some embodiment, an abutment member 63 is configured to couple with the head section 65 so as to align the interproximal-side surface area 415 with the interproximal-side surface area 115. In some embodiment, an abutment member 63 is configured to couple with the head section 65 so as to align the lingual-side surface area 425 with the lingual-side surface area 125. In some embodiment, an abutment member 63 is configured to couple with the head section 65 so as to align the interproximal-side surface area 430 with the interproximal-side surface area 130.

In some embodiments, the facial-side surface area 420 and/or the lingual-side surface area 425 provide an area for bone growth therein to compensate for jawbone deterioration adjacent to the abutment member 63 due to craniofacial growth. In some embodiments, the facial-side surface area 420 and/or the narrower lingual-side surface area 425 provide an arch shaped area for bone growth therein to compensate for jawbone deterioration adjacent to abutment member 63 due to craniofacial growth. In some embodiments, the facial-side surface area 420 and/or the narrower lingual-side surface area 425 provide a flat area for bone growth to compensate for jawbone deterioration adjacent to abutment member 63 due to craniofacial growth. In some embodiments, the facial-side surface area 420 and/or the narrower lingual-side surface area 425 provide a concave shaped area for bone growth therein to compensate for jawbone deterioration adjacent to abutment member 63 due to craniofacial growth. Increasing bone volume and/or soft tissue volume adjacent to the facial-side surface area 420 and/or the narrower lingual-side surface area 425 prevents early exposure of the abutment member 63.

In some embodiments, the facial-side surface area 420 and/or the lingual-side surface area 425 provide a concave shaped area to improve bone formation due to the gap between the existing bone and the facial-side surface area 420 and/or the lingual-side surface area 425. In some embodiments, the facial-side surface area 420 and/or the lingual-side surface area 425 provide a concave shaped area to allow greater bone growth therein. In some embodiments, the facial-side surface area 420 and/or the lingual-side surface area 425 provide a concave shaped area to prevent/minimize pressure between the bone and the abutment member 63 during and/or immediately after the procedure. Preventing and/or minimizing pressure between the bone and the abutment member 63 during and/or immediately after the procedure prevent resorption of the bone around the abutment member 63 and/or allows increased bone formation around the abutment member 63. In some embodiments, the facial-side surface area 420 and/or the lingual-side surface area 425 provide a concave shaped area to allow bone and/or soft tissue growth therein.

Figure 6:
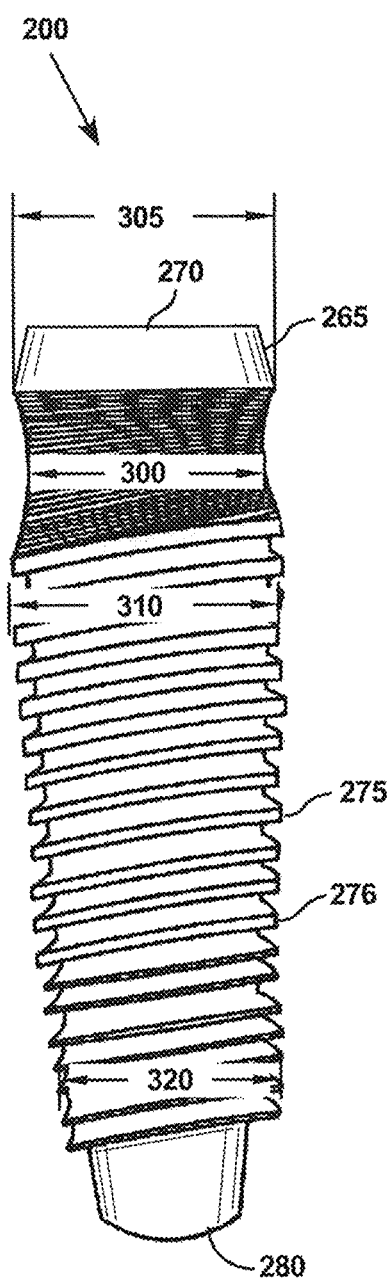
FIG. 6 depicts another dental implant fixture according to some embodiments of the present disclosure.

Referring to FIG. 6, a dental implant fixture 200 is shown according to the present disclosure. In some embodiments presently disclosed, the dental implant fixture 200 comprises a head section 265 with a proximal end 270. In some embodiments, the fixture 200 comprises an elongated shaft section 275 with a distal end 280. In some embodiments, the head section 265 is integrally coupled with the shaft section 275 to form a one-piece implant fixture 200. This prevents bacteria or other infection growth between the head section and the shaft section of the implant fixture 200. In some embodiments, the elongated shaft section 275 is tapered.

Referring to FIG. 6, in some embodiments, the head section 265 is substantially circular comprising a first head section diameter 300 adjacent to the shaft section 275 and comprising a second head section diameter 305 adjacent to the proximal end 270. In some embodiments, the shaft section 275 is substantially circular comprising a first shaft diameter 310 adjacent to the head section 265 and comprising a second shaft diameter 320 adjacent to the distal end 280.

In some embodiments, the first head section diameter 300 is less than the first shaft diameter 310. In some embodiments, the second head section diameter 305 is less than the first shaft diameter 310. In some embodiments, the first head section diameter 300 and the second head section diameter 305 are less than the first shaft diameter 310. In some embodiments, the first head section diameter 300 and the second head section diameter 305 are substantially equal to the first shaft diameter 310. In some embodiments, the second head section diameter 305 is substantially equal to the first shaft diameter 310. In some embodiments, the first shaft diameter 310 is substantially equal to the second shaft diameter 320. In some embodiments, the second shaft diameter 320 is less than the first shaft diameter 310.

In some embodiments, the head section 265 provides an area for bone growth therein to compensate for jawbone deterioration adjacent to the implant fixture 200 due to craniofacial growth. In some embodiments, the head section 265 provides an arch shaped area for bone growth therein to compensate for jawbone deterioration adjacent to the implant fixture 200 due to craniofacial growth. In some embodiments, the head section 265 provides a concave shaped area to allow bone growth therein to compensate for jawbone deterioration adjacent to the implant fixture 200 due to craniofacial growth. Increasing bone volume and/or soft tissue volume adjacent to the head section 265 prevents early exposure of the dental implant fixture 200.

In some embodiments, the head section 265 provides a concave shaped area to improve bone formation due to the gap between the existing bone and the concave shaped area. In some embodiments, the head section 265 provides a concave shaped area to allow greater bone growth therein. In some embodiments, the head section 265 provides a concave shaped area to prevent/minimize pressure between the bone and the head section 265 during and/or immediately after the procedure. Preventing and/or minimizing pressure between the bone and the head section 265 during and/or immediately after the procedure prevent resorption of the bone around the head section 265 and/or allows increased bone formation around the head section 265. In some embodiments, the head section 265 provides a concave shaped area to allow bone and/or soft tissue growth therein.

In some embodiments, the shaft section 275 comprises an outer screw thread 276 extending along at least a portion of its length. In some embodiments, the outer screw thread 276 is continuous. In some embodiments, the outer screw thread 276 is V-Thread, Square Thread, Buttress Thread, Reverse Buttress Thread or a combination of two or more of these threads. In some embodiments, the shaft section 275 comprises a substantially longitudinal groove (not shown) extending from the distal end 280 towards the head section 265. The longitudinal groove (not shown) provides a greater surface area into which bone growth is formed to prevent the implant fixture 200 from vertical and rotational movements within the jawbone.

Referring to FIGS. 7*a-c*, a dental implant fixture 800 is shown according to the present disclosure. In some embodiments presently disclosed, the dental implant fixture 800 comprises a head section 865 with a proximal end 870. In some embodiments, the fixture 800 comprises an elongated shaft section 875 with a distal end 881. In some embodiments, the head section 865 is integrally coupled with the shaft section 875 to form a one-piece implant fixture 800. This prevents bacteria or other infection growth between the head section and the shaft section of the implant fixture 800. In some embodiments, the elongated shaft section 875 is tapered.

In some embodiments, the implant fixture 800 comprises a stepped interior closed bore 880 extending partially downward from the proximal end 870 into the shaft section 875 as shown in FIG. 7*c*. In some embodiments, the stepped interior closed bore 880 is off-center. In some embodiments, the interior closed bore 880 comprises inner screw threads 885 along at least a portion of its length and an annular shelf 890 located above the inner screw threads 885 (as shown in FIG. 7*c*). In some embodiment, the inner screw threads 885 are configured to accommodate the outer screw threads 304 of the bolt member 62. In some embodiments, the stepped interior closed bore 880 is configured to accommodate a protruding engagement end 307 (described in more detail above) of the abutment member 63.

Referring to FIG. 7*b*, a top plan view of the implant fixture 800 is shown according to some embodiments presently disclosed. In some embodiments, the proximal end 870 has a circular flat surface 895 surrounded by a periphery surface 900 comprising a long-axis and a short axis. In some embodiments, the proximal end 870 further comprises two or more apertures 805, 810, 811 for accommodating small tips of a standard dental tool, for example, implant mount or hand driver for orienting the implant fixture 800. In some embodiments, the head section 865 comprises at least one narrower facial-side surface area 820 and at least one wider surface area 830. The facial-side surface area 820 accommodates the contour of the gingival tissue at the facial-side of the patient's oral cavity, which is located adjacent to the interior surface of the patient's lip, while the surface area 830 accommodates the contour of the gingival tissue at the interproximal-side of the patient's oral cavity which is located adjacent to the patient's other tooth and/or implant. In some embodiments, the surface area 830 accommodates the contour of the gingival tissue at the lingual-side of the patient's oral cavity which is located adjacent to the patient's tongue or palate. In some embodiments, the surface area 830 accommodates the contour of the gingival tissue at the lingual-side of the patient's oral cavity which is located adjacent to the patient's tongue or palate and accommodates the contour of the gingival tissue at the interproximal-side of the patient's oral cavity which is located adjacent to the patient's other tooth and/or implant(s). In some embodiments, the facial-side surface area 820 is concaved toward the center of the implant fixture 800.

In some embodiments, the facial-side surface area 820 provides an area for bone growth therein to compensate for jawbone deterioration adjacent to the implant fixture 800 due to craniofacial growth. In some embodiments, the facial-side surface area 820 provides an arch shaped area for bone growth therein to compensate for jawbone deterioration adjacent to the implant fixture 800 due to craniofacial growth. In some embodiments, the facial-side surface area 820 provides a flat area for bone growth to compensate for jawbone deterioration adjacent to the implant fixture 800 due to craniofacial growth. In some embodiments, the facial-side surface area 820 provides a concave shaped area for bone growth therein to compensate for jawbone deterioration adjacent to the implant fixture 800 due to craniofacial growth. Increasing bone volume and/or soft tissue volume adjacent to the facial-side surface area 820 prevents early exposure of the implant fixture 800.

In some embodiments, the facial-side surface area 820 provides a concave shaped area to improve bone formation due to the gap between the existing bone and the facial-side surface area 820. In some embodiments, the facial-side surface area 820 provides a concave shaped area to allow greater bone growth therein. In some embodiments, the facial-side surface area 820 provides a concave shaped area to prevent/minimize pressure between the bone and the implant fixture 800 during and/or immediately after the procedure. Preventing and/or minimizing pressure between the bone and the implant fixture 800 during and/or immediately after the procedure prevent resorption of the bone around the implant fixture 800 and/or allows increased bone formation around the implant fixture 800. In some embodiments, the facial-side surface area 820 provides a concave shaped area to allow bone and/or soft tissue growth therein.

In some embodiments, the dental implant fixture 800 does not comprise the longitudinal groove 36 (shown in FIGS. 2a-b) to prevent bone growth therein so as to allow the dental implant fixture 800 to be removed with less damage to patient's jawbone. In some embodiments, the facial-side surface area 820 provides an area where bone growth can grow therein to prevent the implant fixture 800 from vertical and rotational movements within the patient's jawbone.

In some embodiments, the shaft section 875 comprises an outer screw thread 876 (shown in FIG. 7a) extending along at least a portion of its length. In some embodiments, the outer screw thread 876 is continuous. In some embodiments, the outer screw thread 876 is V-Thread, Square Thread, Buttress Thread, Reverse Buttress Thread or a combination of two or more of these threads. In some embodiments, the shaft section 875 comprises a substantially longitudinal groove or back cut (not shown) extending from the distal end 881 towards the head section 865. The longitudinal groove (not shown) provides a greater surface area into which bone growth is formed to prevent the implant fixture 800 from vertical and rotational movements within the jawbone.

Figure 8:
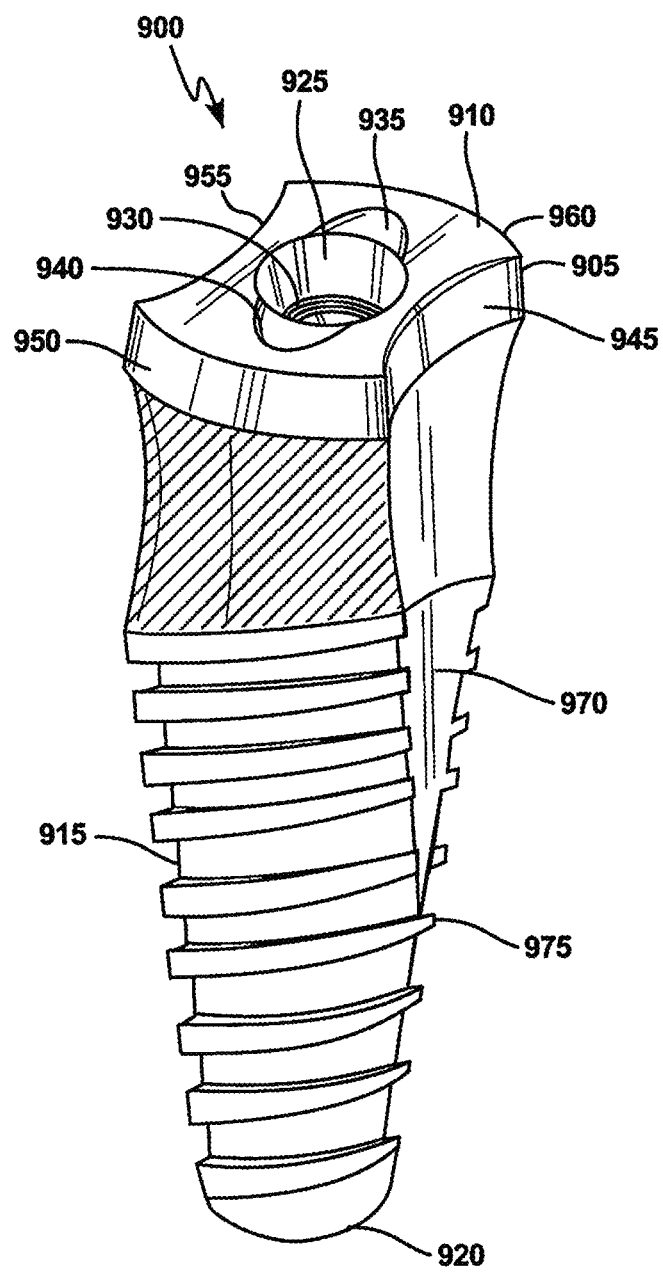
FIG. 8 depicts a dental implant fixture according to some embodiments of the present disclosure.

Referring to FIG. 8, a dental implant fixture 900 is shown according to the present disclosure. In some embodiments presently disclosed, the dental implant fixture 900 comprises a head section 905 with a proximal end 910. In some embodiments, the fixture 900 comprises an elongated shaft section 915 with a distal end 920. In some embodiments, the head section 905 is integrally coupled with the shaft section 915 to form a one-piece implant fixture 900. This prevents bacteria or other infection growth between the head section and the shaft section of the implant fixture 900. In some embodiments, the elongated shaft section 915 is tapered.

In some embodiments, the implant fixture 900 comprises a stepped interior closed bore 925 extending partially downward from the proximal end 910 into the shaft section 915. In some embodiments, the stepped interior closed bore 925 is off-center. In some embodiments, the interior closed bore 925 comprises inner screw threads 930 along at least a portion of its length. In some embodiment, the inner screw threads 930 are configured to accommodate the outer screw threads 304 of the bolt member 62. In some embodiments, the stepped interior closed bore 925 is configured to accommodate a protruding engagement end 307 (described in more detail above) of the abutment member 63. Although the interior closed bore 925 is shown as being circular, it is to be understood that the interior closed bore 925 can be any shape as discussed further below with respect to FIG. 9.

In some embodiments, the proximal end 910 comprises two or more apertures 935, 940 for accommodating small tips of a standard dental tool, for example, implant mount or hand driver for orienting the implant fixture 900. In some embodiments, the head section 905 comprises at least one narrower facial-side surface area 945 and at least one wider interproximal-side surface area 950. The facial-side surface area 945 accommodates the contour of the gingival tissue at the facial-side of the patient's oral cavity, which is located adjacent to the interior surface of the patient's lip, while the interproximal-side surface area 950 accommodates the contour of the gingival tissue at the interproximal-side of the patient's oral cavity which is located adjacent to the patient's other tooth and/or implant. In some embodiments, the facial-side surface area 945 is concaved toward the center of the bore 925.

In some embodiments, the head section 905 comprises a narrower lingual-side surface area 955 and at least one wider interproximal-side surface area 960. The lingual-side surface area 955 accommodates the contour of the gingival tissue at the lingual-side of the patient's oral cavity which is located adjacent to the patient's tongue or palate, while the interproximal-side surface area 960 accommodates the contour of the gingival tissue at the interproximal-side of the patient's oral cavity which is located adjacent to the patient's other tooth and/or implant. In some embodiments, the lingual-side surface area 955 is concaved toward the center of the bore 925.

In some embodiments, the facial-side surface area 945 and/or the lingual-side surface area 955 provide an area for bone growth therein to compensate for jawbone deterioration adjacent to the implant fixture 900 due to craniofacial growth. In some embodiments, the facial-side surface area 945 and/or the narrower lingual-side surface area 955 provide an arch shaped area for bone growth therein to compensate for jawbone deterioration adjacent to the implant fixture 900 due to craniofacial growth. In some embodiments, the facial-side surface area 945 and/or the narrower lingual-side surface area 955 provide a flat area for bone growth to compensate for jawbone deterioration adjacent to the implant fixture 900 due to craniofacial growth. In some embodiments, the facial-side surface area 945 and/or the narrower lingual-side surface area 955 provide a concave shaped area for bone growth therein to compensate for jawbone deterioration adjacent to the implant fixture 900 due to craniofacial growth. Increasing bone volume and/or soft tissue volume adjacent to the facial-side surface area 945 and/or the narrower lingual-side surface area 955 prevents early exposure of the implant fixture 900.

In some embodiments, the facial-side surface area 945 and/or the lingual-side surface area 955 provide a concave shaped area to improve bone formation due to the gap between the existing bone and the facial-side surface area 945 and/or the lingual-side surface area 955. In some embodiments, the facial-side surface area 945 and/or the lingual-side surface area 955 provide a concave shaped area to allow greater bone growth therein. In some embodiments, the facial-side surface area 945 and/or the lingual-side surface area 955 provide a concave shaped area to prevent/minimize pressure between the bone and the head section 905 during and/or immediately after the procedure. Preventing and/or minimizing pressure between the bone and the head section 905 during and/or immediately after the procedure prevent resorption of the bone around the head section 905 and/or allows increased bone formation around the head section 905. In some embodiments, the facial-side surface area 945 and/or the lingual-side surface area 955 provide a concave shaped area to allow bone and/or soft tissue growth therein.

In some embodiments, the dental implant fixture 900 comprises a longitudinal groove 970 to allow bone growth therein to prevent the implant fixture 900 from vertical and rotational movements within the patient's jawbone. In some embodiments, the facial-side surface area 945 and/or the lingual-side surface area 955 provide an area where bone growth can grow therein to prevent the implant fixture 900 from vertical and rotational movements within the patient's jawbone.

In some embodiments, the shaft section 915 comprises an outer screw thread 975 extending along at least a portion of its length. In some embodiments, the outer screw thread 975 is continuous. In some embodiments, the outer screw thread 975 is V-Thread, Square Thread, Buttress Thread, Reverse Buttress Thread or a combination of two or more of these threads. In some embodiments, the shaft section 915 comprises a substantially longitudinal groove or back cut (not shown) extending from the distal end 920 towards the head section 905. The longitudinal groove (not shown) provides a greater surface area into which bone growth is formed to prevent the implant fixture 900 from vertical and rotational movements within the jawbone.

Figure 9:
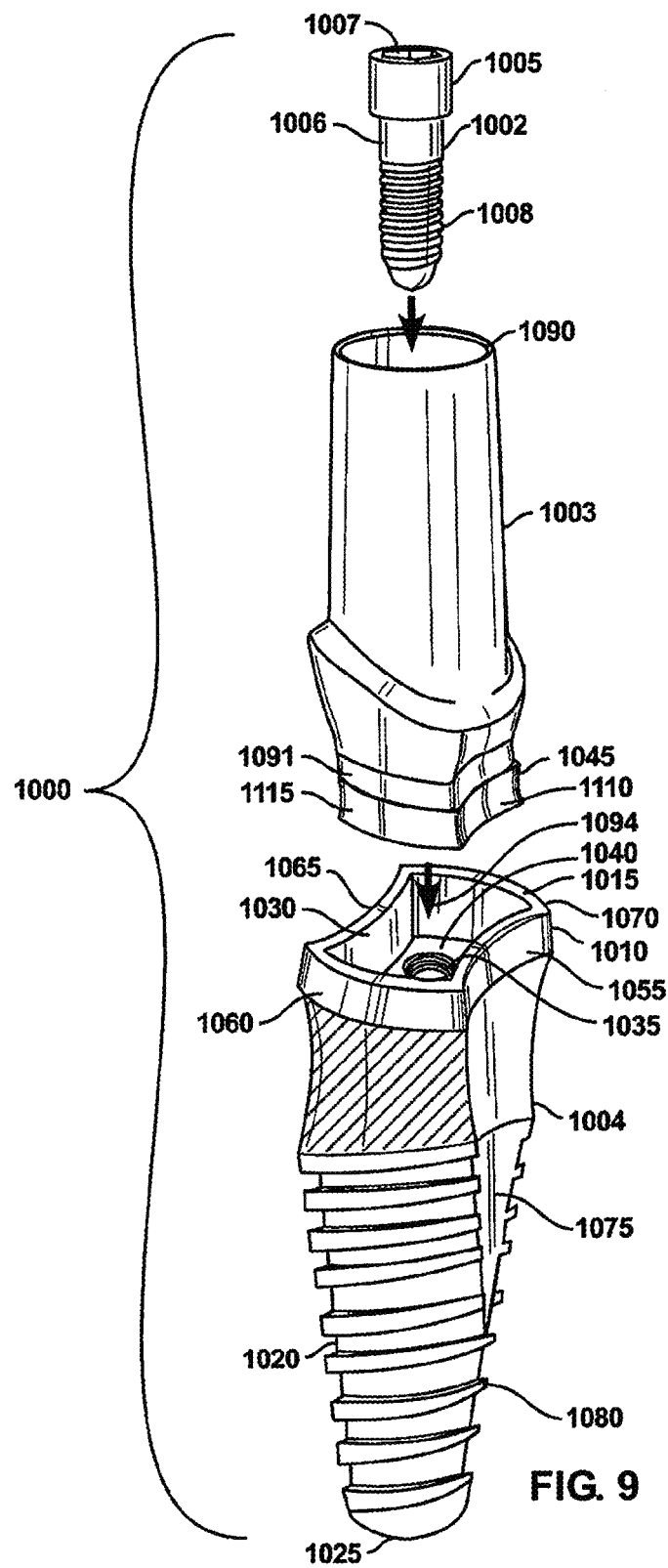
FIG. 9 depicts a dental implant system according to some embodiments of the present disclosure.

Referring to FIG. 9, a dental implant system 1000 is shown according to the present disclosure. In some embodiments, the dental implant system 1000 comprises a bolt member 1002, an abutment member 1003, and a dental implant fixture 1004.

In some embodiments, the bolt member 1002 comprises a head segment 1005 and a shaft segment 1006. In some embodiments, the head segment 1005 is generally disc shaped with a top notch 1007 or any other suitable means to accommodate a driving tool, for example, a screwdriver or any other tool for rotating the bolt member 1002. In some embodiments, the shaft segment 1006 has one end coupled with the head segment 1005. In some embodiments, the shaft segment 1006 comprises an outer screw threads 1008 which are located opposite from the head segment 1005 and extend along at least a portion of its length.

Referring to FIG. 9, in some embodiments presently disclosed, the dental implant fixture 1004 comprises a head section 1010 with a proximal end 1015. In some embodiments, the fixture 1004 comprises an elongated shaft section 1020 with a distal end 1025. In some embodiments, the head section 1010 is integrally coupled with the shaft section 1020 to form a one-piece implant fixture 1004. This prevents bacteria or other infection growth between the head section and the shaft section of the implant fixture 1004. In some embodiments, the elongated shaft section 1020 is tapered.

In some embodiments, the implant fixture 1004 comprises a stepped interior closed bore 1030 extending partially downward from the proximal end 1015 into the shaft section 1020. In some embodiments, the stepped interior closed bore 1030 is off-center. In some embodiments, the interior closed bore 1030 comprises inner screw threads 1035 along at least a portion of its length and an annular shelf 1040 located above the inner screw threads 1035 (as shown in FIG. 9). In some embodiments, the inner screw threads 1035 are configured to accommodate the outer screw threads 1008 of the bolt member 1002. In some embodiments, the stepped interior closed bore 1030 is configured to accommodate a protruding engagement end 1045 (described in more detail below) of the abutment member 1003.

Figure 10:
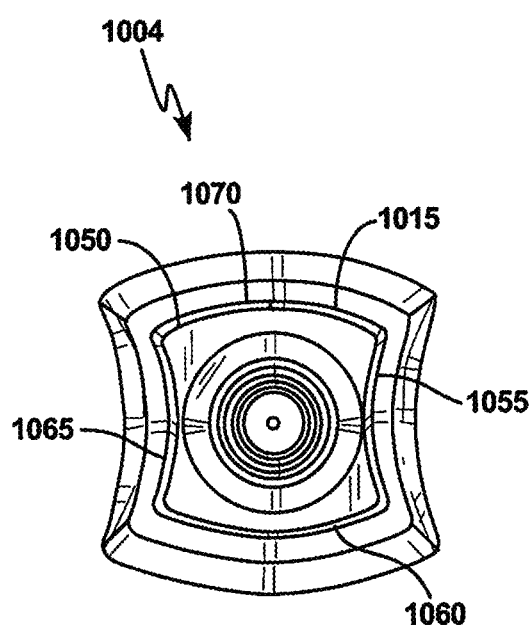
FIG. 10 depicts a top plan view of the dental implant fixture shown in FIG. 9.

Referring to FIG. 10, a top plan view of the implant fixture 1004 is shown according to some embodiments presently disclosed. In some embodiments, the proximal end 1015 has a periphery surface 1050 comprising a long-axis and a short axis. In some embodiments, the stepped interior closed bore 1030 is configured to accommodate a dental tool for orienting the implant fixture 1004. In some embodiments, the head section 1010 comprises at least one narrower facial-side surface area 1055 and at least one wider interproximal-side surface area 1060. The facial-side surface area 1055 accommodates the contour of the gingival tissue at the facial-side of the patient's oral cavity, which is located adjacent to the interior surface of the patient's lip, while the interproximal-side surface area 1060 accommodates the contour of the gingival tissue at the interproximal-side of the patient's oral cavity which is located adjacent to the patient's other tooth and/or implant. In some embodiments, the facial-side surface area 1055 is concaved toward the center of the interior closed bore 1030.

In some embodiments, the head section 1010 comprises a narrower lingual-side surface area 1065 and at least one wider interproximal-side surface area 1070. The lingual-side surface area 1065 accommodates the contour of the gingival tissue at the lingual-side of the patient's oral cavity which is located adjacent to the patient's tongue or palate, while the interproximal-side surface area 1070 accommodates the contour of the gingival tissue at the interproximal-side of the patient's oral cavity which is located adjacent to the patient's other tooth and/or implant. In some embodiments, the lingual-side surface area 1065 is concaved toward the center of the interior closed bore 1030.

In some embodiments, the facial-side surface area 1055 and/or the lingual-side surface area 1065 provide an area for bone growth therein to compensate for jawbone deterioration adjacent to the implant fixture 1004 due to craniofacial growth. In some embodiments, the facial-side surface area 1055 and/or the narrower lingual-side surface area 1065 provide an arch shaped area for bone growth therein to compensate for jawbone deterioration adjacent to the implant fixture 1004 due to craniofacial growth. In some embodiments, the facial-side surface area 1055 and/or the narrower lingual-side surface area 1065 provide a flat area for bone growth to compensate for jawbone deterioration adjacent to the implant fixture 1004 due to craniofacial growth. In some embodiments, the facial-side surface area 1055 and/or the narrower lingual-side surface area 1065 provide a concave shaped area for bone growth therein to compensate for jawbone deterioration adjacent to the implant fixture 1004 due to craniofacial growth. Increasing bone volume and/or soft tissue volume adjacent to the facial-side surface area 1055 and/or the narrower lingual-side surface area 1065 prevents early exposure of the implant fixture 1004.

In some embodiments, the facial-side surface area 1055 and/or the lingual-side surface area 1065 provide a concave shaped area to improve bone formation due to the gap between the existing bone and the facial-side surface area 1055 and/or the lingual-side surface area 1065. In some embodiments, the facial-side surface area 1055 and/or the lingual-side surface area 1065 provide a concave shaped area to allow greater bone growth therein. In some embodiments, the facial-side surface area 1055 and/or the lingual-side surface area 1065 provide a concave shaped area to prevent/minimize pressure between the bone and the head section 1010 during and/or immediately after the procedure. Preventing and/or minimizing pressure between the bone and the head section 1010 during and/or immediately after the procedure prevent resorption of the bone around the head section 1010 and/or allows increased bone formation around the head section 1010. In some embodiments, the facial-side surface area 155 and/or the lingual-side surface area 165 provide a concave shaped area to allow bone and/or soft tissue growth therein.

In some embodiments, the dental implant fixture 1004 does not comprise the longitudinal groove 36 (shown in FIGS. 2*a-b*) to prevent bone growth therein so as to allow the dental implant fixture 1004 to be removed with less damage to patient's jawbone. In some embodiments, the dental implant fixture 1004 comprises a longitudinal groove 1075 to allow bone growth therein. In some embodiments, the facial-side surface area 1055 and/or the lingual-side surface area 1065 provide an area where bone growth can grow therein to prevent the implant fixture 1004 from vertical and rotational movements within the patient's jawbone.

In some embodiments, the shaft section 1020 comprises an outer screw thread 1080 extending along at least a portion of its length. In some embodiments, the outer screw thread 1080 is continuous. In some embodiments, the outer screw thread 1080 is V-Thread, Square Thread, Buttress Thread, Reverse Buttress Thread or a combination of two or more of these threads. In some embodiments, the shaft section 1020 comprises a substantially longitudinal groove or back cut (not shown) extending from the distal end 1025 towards the head section 1010. The longitudinal groove (not shown) provides a greater surface area into which bone growth is formed to prevent the implant fixture 1004 from vertical and rotational movements within the jawbone.

Referring to FIG. 9, in some embodiments, an abutment member 1003 comprises a distal end 1090 with, for example, a circular opening to accommodate the shaft segment 1006 of the bolt member 1002. Referring to FIG. 9, in some embodiments, an abutment member 1002 comprises a proximal portion 1091 with a protruding engagement end 1045 extending there from.

Figure 11:
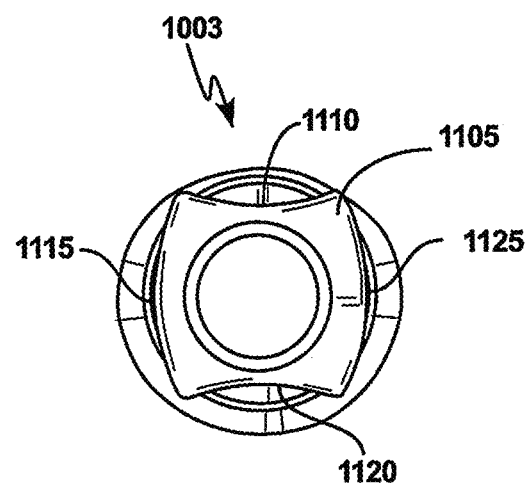
FIG. 11 depicts a bottom plan view of an abutment member according to some embodiments of the present disclosure.

Referring to FIG. 11, a bottom plan view of the abutment member 1003 is shown according to some embodiments presently disclosed. According to some embodiments, the protruding engagement end 1045 comprises a surface 1105. In some embodiments, the surface 1105 comprises a long-axis and a short axis. In some embodiments, the protruding engagement end 1045 comprises at least one narrower facial-side surface area 1110 and at least one wider interproximal-side surface area 1115. In some embodiments, the facial-side surface area 1110 is substantially similar to the facial-side surface area 1055. In some embodiments, the interproximal-side surface area 1115 is substantially similar to the interproximal-side surface area 1060. In some embodiments, the facial-side surface area 1110 is concaved toward the center of the abutment member 1003.

In some embodiments, the protruding engagement end 1045 comprises a narrower lingual-side surface area 1120 and at least one wider interproximal-side surface area 1125. In some embodiments, the lingual-side surface area 1120 is substantially similar to the lingual-side surface area 1065. In some embodiments, the interproximal-side surface area 1125 is substantially similar to the interproximal-side surface area 1070. In some embodiments, the lingual-side surface area 1120 is concaved toward the center of the abutment member 1003.

In some embodiment, an abutment member 1003 is configured to couple with the head section 1010 as shown in FIG. 9 by arrow 1094. In some embodiment, an abutment member 1003 is configured to couple with the head section 1010 so as to align the facial-side surface area 1110 with the facial-side surface area 1055. In some embodiment, an abutment member 1003 is configured to couple with the head section 1010 so as to align the lingual-side surface area 1120 with the lingual-side surface area 1065.

In some embodiments, the facial-side surface area 1110 and/or the lingual-side surface area 1120 provide a concave shaped area for bone and soft tissue formation therein to compensate for jawbone deterioration adjacent to the abutment member 1003 due to craniofacial growth. In some embodiments, the facial-side surface area 1110 and/or the narrower lingual-side surface area 1120 provide an arch shaped area for bone growth and soft tissue formation therein to compensate for jawbone deterioration adjacent to abutment member 1003 due to craniofacial growth. In some embodiments, the facial-side surface area 1110 and/or the narrower lingual-side surface area 1120 provide a flat area for bone growth and soft tissue formation to compensate for jawbone deterioration adjacent to abutment member 1003 due to craniofacial growth. In some embodiments, the facial-side surface area 1110 and/or the narrower lingual-side surface area 1120 provide a concave shaped area for bone and soft tissue formation therein to compensate for jawbone deterioration adjacent to abutment member 1003 due to craniofacial growth. Increasing bone volume and/or soft tissue volume adjacent to the facial-side surface area 1110 and/or the narrower lingual-side surface area 1120 prevents early exposure of the abutment member 1003.

In some embodiments, the facial-side surface area 1110 and/or the lingual-side surface area 1120 provide a concave shaped area to improve bone formation due to the gap between the existing bone and the facial-side surface area 1110 and/or the lingual-side surface area 1120. In some embodiments, the facial-side surface area 1110 and/or the lingual-side surface area 1120 provide a concave shaped area to allow greater bone growth therein. In some embodiments, the facial-side surface area 1110 and/or the lingual-side surface area 1120 provide a concave shaped area to prevent/minimize pressure between the bone and the abutment member 1003 during and/or immediately after the procedure. Preventing and/or minimizing pressure between the bone and the abutment member 1003 during and/or immediately after the procedure prevent resorption of the bone around the abutment member 1003 and/or allows increased bone formation around the abutment member 1003. In some embodiments, the facial-side surface area 1110 and/or the lingual-side surface area 1120 provide a concave shaped area to allow bone and/or soft tissue growth therein.

Figure 12A:
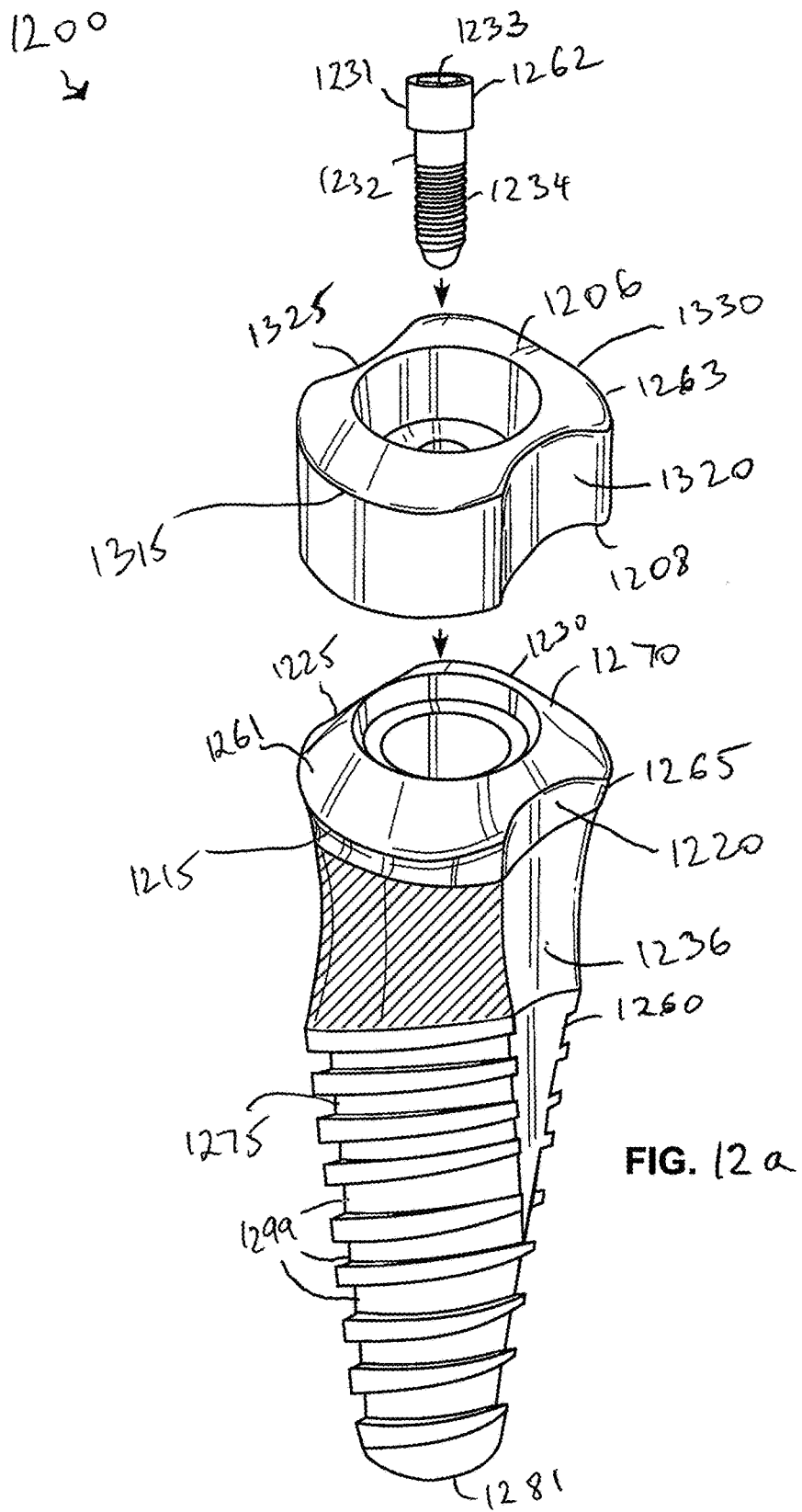
Figure 12B:
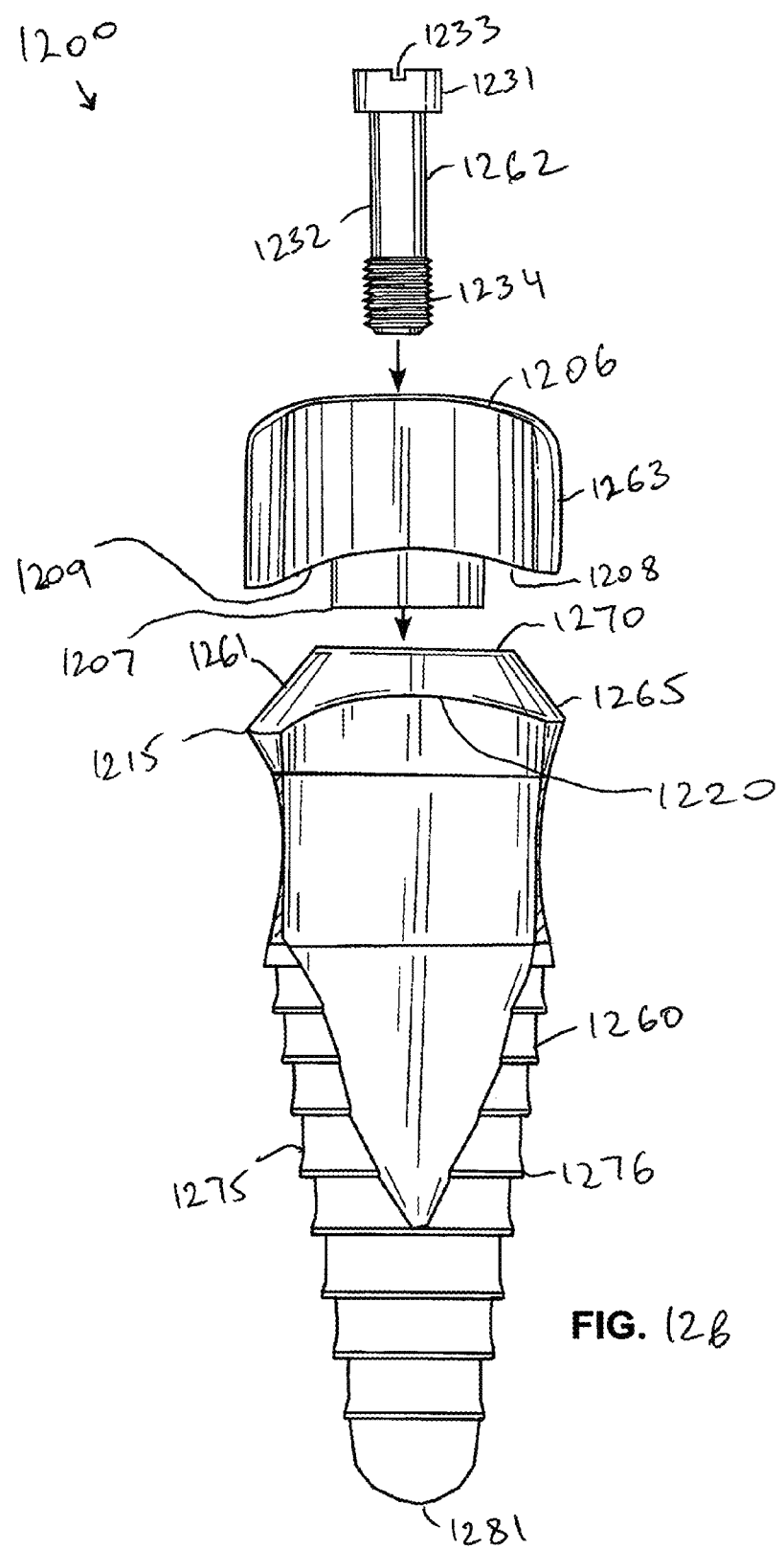

Referring to FIGS. 12a-b, a dental implant system 1200 is shown according to the present disclosure. In some embodiments, the dental implant system 1200 comprises a bolt member 1262, a healing cap 1263, and a dental implant fixture 1260. According to some embodiments, the dental implant system 1200 further comprises an abutment member (not shown).

In some embodiments, the bolt member 1262 comprises a head segment 1231 and a shaft segment 1232. In some embodiments, the head segment 1231 is generally disc shaped with a top notch 1233 or any other suitable means to accommodate a driving tool, for example, a screwdriver or any other tool for rotating the bolt member 1262. In some embodiments, the shaft segment 1232 has one end coupled with the head segment 1231. In some embodiments, the shaft segment 1232 comprises an outer screw threads 1234 which are located opposite from the head segment 1231 and extend along at least a portion of its length.

Referring to FIGS. 12a-b, a dental implant fixture 1260 is shown according to the present disclosure. In some embodiments presently disclosed, the dental implant fixture 1260 comprises a head section 1265 with a proximal end 1270. In some embodiments, the fixture 1260 comprises an elongated shaft section 1275 with a distal end 1281. In some embodiments, the head section 1265 is integrally coupled with the shaft section 1275 to form a one-piece implant fixture 1260. This prevents bacteria or other infection growth between the head section and the shaft section of the implant fixture 1260. In some embodiments, the elongated shaft section 1275 is tapered. According to some embodiments, the head section 1265 is eliptically shaped. According to some embodiments, the head section 1265 is triangularly shaped. According to some embodiments, the head section 1265 is circularly shaped.

In some embodiments, the implant fixture 1260 comprises a stepped interior closed bore 1280 extending partially downward from the proximal end 1270 into the shaft section 1275. In some embodiments, the stepped interior closed bore 1280 is off-center. In some embodiments, the interior closed bore 1280 comprises inner screw threads (not shown) along at least a portion of its length and an annular shelf (not shown) located above the inner screw threads (not shown). In some embodiment, the inner screw threads (not shown) are configured to accommodate the outer screw threads 1234 of the bolt member 1262.

Referring to FIGS. 12a-c, in some embodiments, the proximal end 1270 has a bevel periphery surface 1261 comprising a long-axis and a short axis. According to some embodiments, the proximal end 1270 has a flat surface 1261 comprising a long-axis and a short axis. In some embodiments, the head section 1265 comprises at least one narrower facial-side surface area 1220 and at least one wider interproximal-side surface area 1215. The facial-side surface area 1220 accommodates the contour of the gingival tissue at the facial-side of the patient's oral cavity, which is located adjacent to the interior surface of the patient's lip, while the interproximal-side surface area 1215 accommodates the contour of the gingival tissue at the interproximal-side of the patient's oral cavity which is located adjacent to the patient's other tooth and/or implant. In some embodiments, the facial-side surface area 1220 is concaved toward the center of the surface 1261.

In some embodiments, the head section 1265 comprises a narrower lingual-side surface area 1225 and at least one wider interproximal-side surface area 1230. The lingual-side surface area 1225 accommodates the contour of the gingival tissue at the lingual-side of the patient's oral cavity which is located adjacent to the patient's tongue or palate, while the interproximal-side surface area 1230 accommodates the contour of the gingival tissue at the interproximal-side of the patient's oral cavity which is located adjacent to the patient's other tooth and/or implant. In some embodiments, the lingual-side surface area 1225 is concaved toward the center of the surface 1261.

In some embodiments, the facial-side surface area 1220 and/or the lingual-side surface area 1225 provide an area for bone growth therein to compensate for jawbone deterioration adjacent to the implant fixture 1260 due to craniofacial growth. In some embodiments, the facial-side surface area 1220 and/or the narrower lingual-side surface area 1225 provide an arch shaped area for bone growth therein to compensate for jawbone deterioration adjacent to the implant fixture 1260 due to craniofacial growth. In some embodiments, the facial-side surface area 1220 and/or the narrower lingual-side surface area 1225 provide a flat area for bone growth to compensate for jawbone deterioration adjacent to the implant fixture 1260 due to craniofacial growth. In some embodiments, the facial-side surface area 1220 and/or the narrower lingual-side surface area 1225 provide a concave shaped area for bone growth therein to compensate for jawbone deterioration adjacent to the implant fixture 1260 due to craniofacial growth. Increasing bone volume and/or soft tissue volume adjacent to the facial-side surface area 1220 and/or the narrower lingual-side surface area 1225 prevents early exposure of the implant fixture 1260.

In some embodiments, the facial-side surface area 1220 and/or the lingual-side surface area 1225 provide a concave shaped area to improve bone formation due to the gap between the existing bone and the facial-side surface area 1220 and/or the lingual-side surface area 1225. In some embodiments, the facial-side surface area 1220 and/or the lingual-side surface area 1225 provide a concave shaped area to allow greater bone growth therein. In some embodiments, the facial-side surface area 1220 and/or the lingual-side surface area 1225 provide a concave shaped area to prevent/minimize pressure between the bone and the head section 1265 during and/or immediately after the procedure. Preventing and/or minimizing pressure between the bone and the head section 1265 during and/or immediately after the procedure prevent resorption of the bone around the head section 1265 and/or allows increased bone formation around the head section 1265. In some embodiments, the facial-side surface area 1220 and/or the lingual-side surface area 1225 provide a concave shaped area to allow bone and/or soft tissue growth therein.

In some embodiments, the dental implant fixture 1260 comprises the longitudinal groove 1236 to allow bone growth therein to prevent the implant fixture 1260 from vertical and rotational movements within the patient's jawbone. In some embodiments, the facial-side surface area 1220 and/or the lingual-side surface area 1225 provide an area where bone growth can grow therein to prevent the implant fixture 1260 from vertical and rotational movements within the patient's jawbone.

In some embodiments, the shaft section 1275 comprises an outer screw thread 1276 (shown in FIG. 12b) extending along at least a portion of its length. In some embodiments, the outer screw thread 1276 is continuous. In some embodiments, the outer screw thread 1276 is V-Thread, Square Thread, Buttress Thread, Reverse Buttress Thread or a combination of two or more of these threads. In some embodiments, the shaft section 1275 comprises a substantially longitudinal groove or back cut (not shown) extending from the distal end 1281 towards the head section 1265. The longitudinal groove (not shown) provides a greater surface area into which bone growth is formed to prevent the implant fixture 1260 from vertical and rotational movements within the jawbone.

In some embodiments, the shaft section 1275 comprises a plurality of spaced apart transverse annular grooves 1299 (shown in FIG. 12*a*) extending along at least a portion of its length to provides a greater surface area into which bone growth is formed to prevent the implant fixture 1260 from vertical and rotational movements within the jawbone.

Referring to FIGS. 12*a-b*, in some embodiments, the healing cap 1263 comprises a distal end 1206 with a circular opening to accommodate the shaft segment 1232 of the bolt member 1262. Referring to FIG. 12*a-b*, in some embodiments, the healing cap 1263 comprises a proximal portion 1208 with a protruding engagement end 1207 extending there from.

According to some embodiments, the proximal portion 1208 comprises a bevel surface 1209. According to some embodiments, the beveled surface 1209 matches perfectly the bevel periphery surface 1261 of proximal end 1270.

According to some embodiments, the proximal portion 1208 comprises a flat surface 1209. According to some embodiments, the flat surface 1209 matches perfectly the flat surface 1261 of proximal end 1270. According to some embodiments, the proximal portion 1208 is eliptically shaped. According to some embodiments, the proximal portion 1208 is triangularly shaped. According to some embodiments, the proximal portion 1208 is circularly shaped.

According to some embodiments, the proximal portion 1208 comprises a surface 1209. According to some embodiments, the surface 1209 matches perfectly the surface 1261 of proximal end 1270.

In some embodiments, the proximal portion 1208 comprises a long-axis and a short axis. In some embodiments, the proximal portion 1208 comprises at least one narrower facial-side surface area 1320 and at least one wider interproximal-side surface area 1315. In some embodiments, the facial-side surface area 1320 is substantially similar to the facial-side surface area 1220. In some embodiments, the interproximal-side surface area 1315 is substantially similar to the interproximal-side surface area 1215. In some embodiments, the facial-side surface area 1320 is concaved toward the center of the healing cap 1263.

In some embodiments, the proximal portion 1208 comprises a narrower lingual-side surface area 1325 and at least one wider interproximal-side surface area 1330. In some embodiments, the lingual-side surface area 1325 is substantially similar to the lingual-side surface area 1225. In some embodiments, the interproximal-side surface area 1330 is substantially similar to the interproximal-side surface area 1230. In some embodiments, the lingual-side surface area 1325 is concaved toward the center of the healing cap 1263.

In some embodiment, the healing cap 1263 is configured to couple with the head section 1265 as shown in FIGS. 12*a-b*. In some embodiment, the healing cap 1263 is configured to couple with the head section 1265 so as to align the facial-side surface area 1320 with the facial-side surface area 1220. In some embodiment, the healing cap 1263 is configured to couple with the head section 1265 so as to align the interproximal-side surface area 1315 with the interproximal-side surface area 1215. In some embodiment, the healing cap 1263 is configured to couple with the head section 1265 so as to align the lingual-side surface area 1325 with the lingual-side surface area 1225. In some embodiment, the healing cap 1263 is configured to couple with the head section 1265 so as to align the interproximal-side surface area 1330 with the interproximal-side surface area 1230.

In some embodiments, the facial-side surface area 1320 and/or the lingual-side surface area 1325 provide an area for bone growth therein to compensate for jawbone deterioration adjacent to the healing cap 1263 due to craniofacial growth. In some embodiments, the facial-side surface area 1320 and/or the narrower lingual-side surface area 1325 provide an arch shaped area for bone growth therein to compensate for jawbone deterioration adjacent to the healing cap 1263 due to craniofacial growth. In some embodiments, the facial-side surface area 1320 and/or the narrower lingual-side surface area 1325 provide a flat area for bone growth to compensate for jawbone deterioration adjacent to the healing cap 1263 due to craniofacial growth. In some embodiments, the facial-side surface area 1320 and/or the narrower lingual-side surface area 1325 provide a concave shaped area for bone growth therein to compensate for jawbone deterioration adjacent to the healing cap 1263 due to craniofacial growth. Increasing bone volume and/or soft tissue volume adjacent to the facial-side surface area 1320 and/or the narrower lingual-side surface area 1325 prevents early exposure of the healing cap 1263.

In some embodiments, the facial-side surface area 1320 and/or the lingual-side surface area 1325 provide a concave shaped area to improve bone formation due to the gap between the existing bone and the facial-side surface area 1320 and/or the lingual-side surface area 1325. In some embodiments, the facial-side surface area 1320 and/or the lingual-side surface area 1325 provide a concave shaped area to allow greater bone growth therein. In some embodiments, the facial-side surface area 1320 and/or the lingual-side surface area 1325 provide a concave shaped area to prevent/minimize pressure between the bone and the healing cap 1263 during and/or immediately after the procedure. Preventing and/or minimizing pressure between the bone and the healing cap 1263 during and/or immediately after the procedure prevent resorption of the bone around the healing cap 1263 and/or allows increased bone formation around the healing cap 1263. In some embodiments, the facial-side surface area 1320 and/or the lingual-side surface area 1325 provide a concave shaped area to allow bone and/or soft tissue growth therein.

Figure 13A:
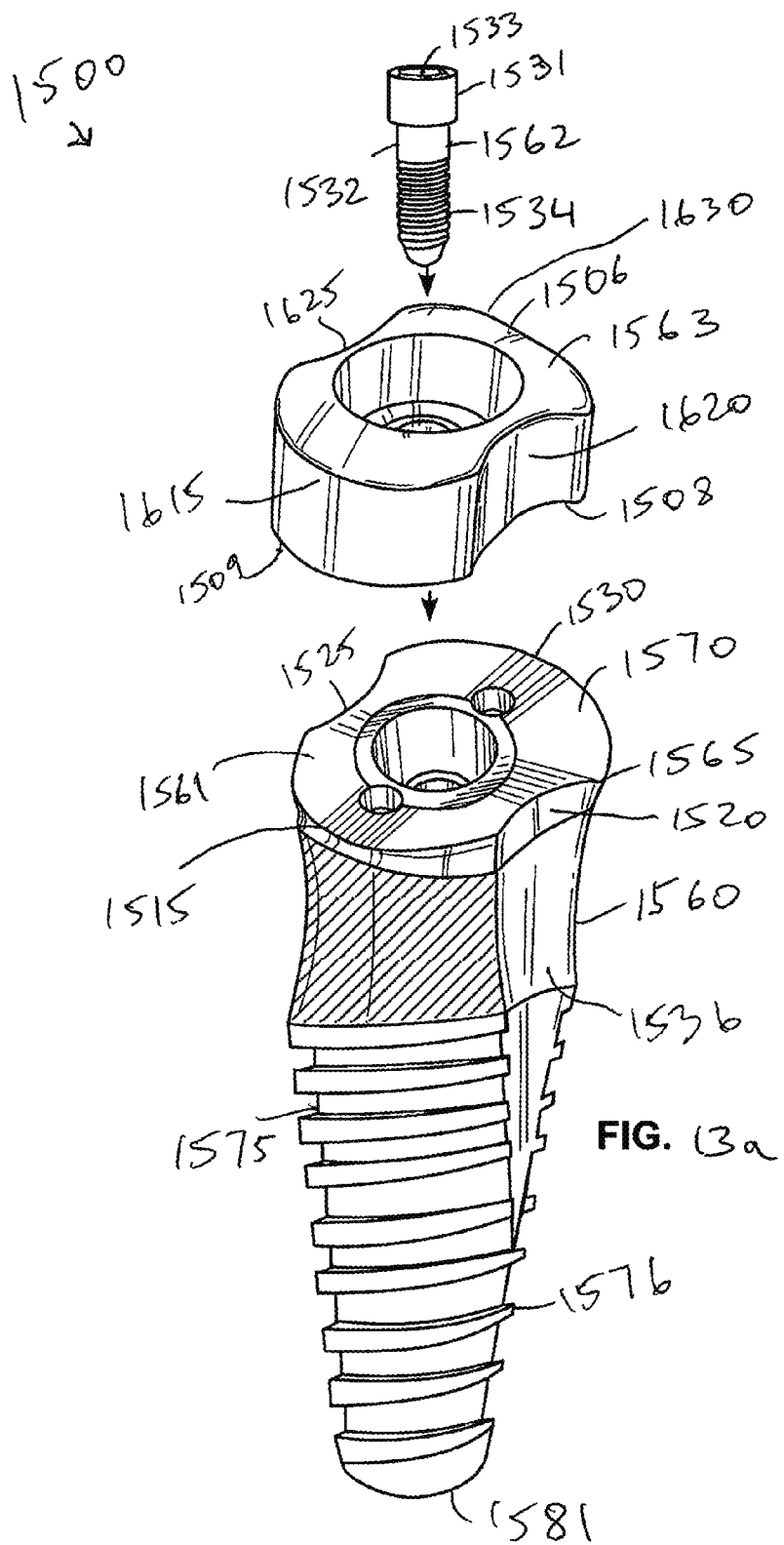
FIG. 13a-b depict another dental implant system according to some embodiments of the present disclosure.
Figure 13B:
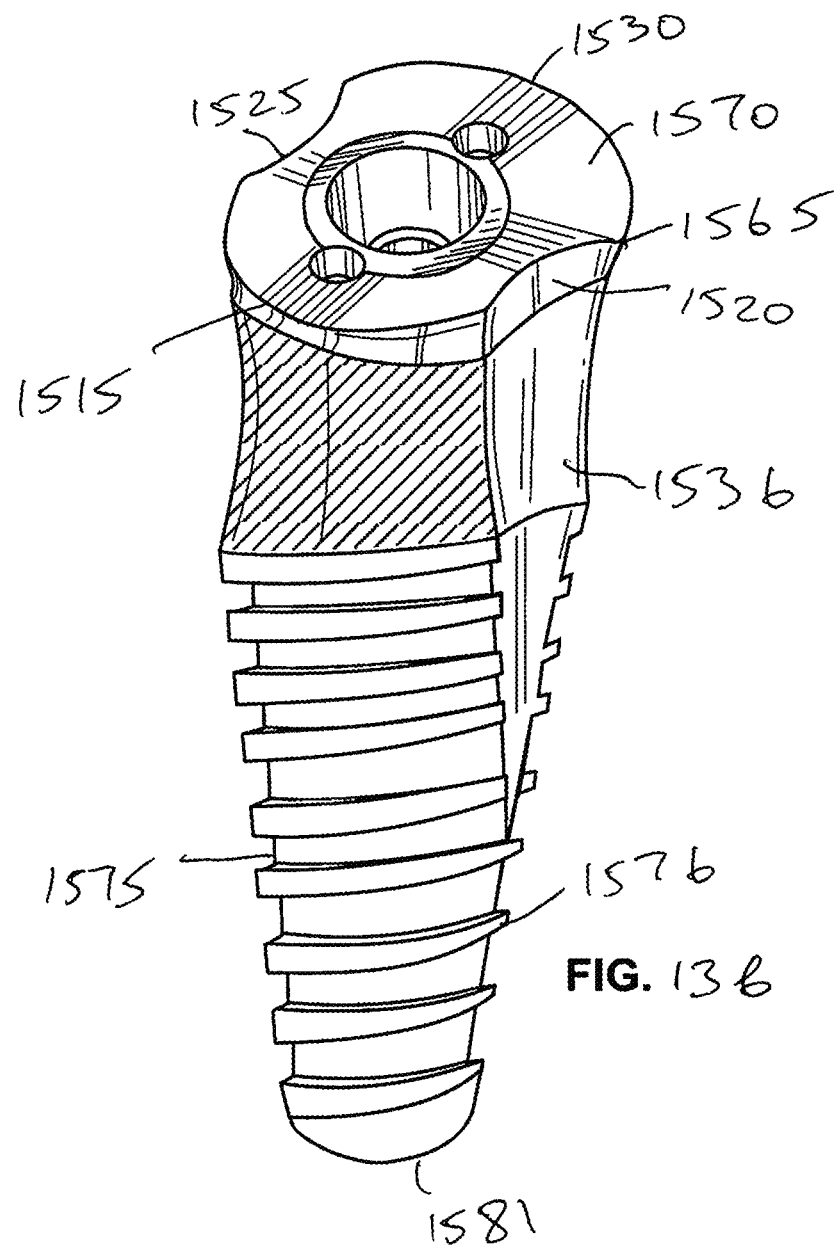

Referring to FIGS. 13*a-b*, a dental implant system 1500 is shown according to the present disclosure. In some embodiments, the dental implant system 1500 comprises a bolt member 1562, a healing cap 1563, and a dental implant fixture 1560. According to some embodiments, the dental implant system 1500 further comprises an abutment member (not shown).

In some embodiments, the bolt member 1562 comprises a head segment 1531 and a shaft segment 1532. In some embodiments, the head segment 1531 is generally disc shaped with a top notch 1533 or any other suitable means to accommodate a driving tool, for example, a screwdriver or any other tool for rotating the bolt member 1562. In some embodiments, the shaft segment 1532 has one end coupled with the head segment 1531. In some embodiments, the shaft segment 1532 comprises an outer screw threads 1534 which are located opposite from the head segment 1531 and extend along at least a portion of its length.

Referring to FIGS. 13*a-b*, a dental implant fixture 1560 is shown according to the present disclosure. In some embodiments presently disclosed, the dental implant fixture 1560 comprises a head section 1565 with a proximal end 1570. In some embodiments, the fixture 1560 comprises an elongated shaft section 1575 with a distal end 1581. In some embodiments, the head section 1565 is integrally coupled with the shaft section 1575 to form a one-piece implant fixture 1560. This prevents bacteria or other infection growth between the head section and the shaft section of the implant fixture 1560. In some embodiments, the elongated shaft section 1575 is tapered. According to some embodiments, the head section 1565 is eliptically shaped. According to some embodiments, the head section 1565 is triangularly shaped. According to some embodiments, the head section 1565 is circularly shaped.

In some embodiments, the implant fixture 1560 comprises a stepped interior closed bore (not shown) extending partially downward from the proximal end 1570 into the shaft section 1575. In some embodiments, the stepped interior closed bore (not shown) is off-center. In some embodiments, the interior closed bore (not shown) comprises inner screw threads (not shown) along at least a portion of its length and an annular shelf (not shown) located above the inner screw threads (not shown). In some embodiment, the inner screw threads (not shown) are configured to accommodate the outer screw threads 1534 of the bolt member 1562.

Referring to FIGS. 13*a-b*, in some embodiments, the proximal end 1570 has a surface 1561 comprising a long-axis and a short axis. According to some embodiments, the surface 1516 is flat. According to some embodiments, the surface 1516 is beveled. In some embodiments, the head section 1565 comprises at least one narrower facial-side surface area 1520 and at least one wider interproximal-side surface area 1515. The facial-side surface area 1520 accommodates the contour of the gingival tissue at the facial-side of the patient's oral cavity, which is located adjacent to the interior surface of the patient's lip, while the interproximal-side surface area 1515 accommodates the contour of the gingival tissue at the interproximal-side of the patient's oral cavity which is located adjacent to the patient's other tooth and/or implant. In some embodiments, the facial-side surface area 1520 is concaved toward the center of the surface 1561.

In some embodiments, the head section 1565 comprises a narrower lingual-side surface area 1525 and at least one wider interproximal-side surface area 1530. The lingual-side surface area 1525 accommodates the contour of the gingival tissue at the lingual-side of the patient's oral cavity which is located adjacent to the patient's tongue or palate, while the interproximal-side surface area 1530 accommodates the contour of the gingival tissue at the interproximal-side of the patient's oral cavity which is located adjacent to the patient's other tooth and/or implant. In some embodiments, the lingual-side surface area 1525 is concaved toward the center of the surface 1561.

In some embodiments, the facial-side surface area 1520 and/or the lingual-side surface area 1525 provide an area for bone growth therein to compensate for jawbone deterioration adjacent to the implant fixture 1560 due to craniofacial growth. In some embodiments, the facial-side surface area 1520 and/or the narrower lingual-side surface area 1525 provide an arch shaped area for bone growth therein to compensate for jawbone deterioration adjacent to the implant fixture 1560 due to craniofacial growth. In some embodiments, the facial-side surface area 1520 and/or the narrower lingual-side surface area 1525 provide a flat area for bone growth to compensate for jawbone deterioration adjacent to the implant fixture 1560 due to craniofacial growth. In some embodiments, the facial-side surface area 1520 and/or the narrower lingual-side surface area 1525 provide a concave shaped area for bone growth therein to compensate for jawbone deterioration adjacent to the implant fixture 1560 due to craniofacial growth. Increasing bone volume and/or soft tissue volume adjacent to the facial-side surface area 1520 and/or the narrower lingual-side surface area 1525 prevents early exposure of the implant fixture 1560.

In some embodiments, the facial-side surface area 1520 and/or the lingual-side surface area 1525 provide a concave shaped area to improve bone formation due to the gap between the existing bone and the facial-side surface area 1520 and/or the lingual-side surface area 1525. In some embodiments, the facial-side surface area 1520 and/or the lingual-side surface area 1525 provide a concave shaped area to allow greater bone growth therein. In some embodiments, the facial-side surface area 1520 and/or the lingual-side surface area 1525 provide a concave shaped area to prevent/minimize pressure between the bone and the head section 1565 during and/or immediately after the procedure. Preventing and/or minimizing pressure between the bone and the head section 1565 during and/or immediately after the procedure prevent resorption of the bone around the head section 1565 and/or allows increased bone formation around the head section 1565. In some embodiments, the facial-side surface area 1520 and/or the lingual-side surface area 1525 provide a concave shaped area to allow bone and/or soft tissue growth therein.

In some embodiments, the dental implant fixture 1560 comprises the longitudinal groove 1536 to allow bone growth therein to prevent the implant fixture 1560 from vertical and rotational movements within the patient's jawbone. In some embodiments, the facial-side surface area 1520 and/or the lingual-side surface area 1525 provide an area where bone growth can grow therein to prevent the implant fixture 1560 from vertical and rotational movements within the patient's jawbone.

In some embodiments, the shaft section 1575 comprises an outer screw thread 1576 (shown in FIGS. 13*a-b*) extending along at least a portion of its length. In some embodiments, the outer screw thread 1576 is continuous. In some embodiments, the outer screw thread 1576 is V-Thread, Square Thread, Buttress Thread, Reverse Buttress Thread or a combination of two or more of these threads. In some embodiments, the shaft section 1575 comprises a substantially longitudinal groove or back cut (not shown) extending from the distal end 1581 towards the head section 1565. The longitudinal groove (not shown) provides a greater surface area into which bone growth is formed to prevent the implant fixture 1560 from vertical and rotational movements within the jawbone.

Referring to FIGS. 13*a-b*, in some embodiments, the healing cap 1563 comprises a distal end 1506 with a circular opening to accommodate the shaft segment 1532 of the bolt member 1562. Referring to FIG. 13*a-b*, in some embodiments, the healing cap 1563 comprises a proximal portion 1508 with a protruding engagement end (not shown) extending there from.

According to some embodiments, the proximal portion 1508 comprises a surface 1509. According to some embodiments, the beveled surface 1509 matches perfectly the surface 1561 of proximal end 1570. According to some embodiments, the proximal portion 1508 is eliptically shaped. According to some embodiments, the proximal portion 1508 is triangularly shaped. According to some embodiments, the proximal portion 1508 is circularly shaped.

In some embodiments, the proximal portion 1508 comprises a long-axis and a short axis. In some embodiments, the proximal portion 1508 comprises at least one narrower facial-side surface area 1620 and at least one wider interproximal-side surface area 1615. In some embodiments, the facial-side surface area 1620 is substantially similar to the facial-side surface area 1520. In some embodiments, the interproximal-side surface area 1615 is substantially similar to the interproximal-side surface area 1515. In some embodiments, the facial-side surface area 1620 is concaved toward the center of the healing cap 1563.

In some embodiments, the proximal portion 1508 comprises a narrower lingual-side surface area 1625 and at least one wider interproximal-side surface area 1630. In some embodiments, the lingual-side surface area 1625 is substantially similar to the lingual-side surface area 1525. In some embodiments, the interproximal-side surface area 1630 is substantially similar to the interproximal-side surface area 1530. In some embodiments, the lingual-side surface area 1625 is concaved toward the center of the healing cap 1563.

In some embodiment, the healing cap 1563 is configured to couple with the head section 1565 as shown in FIG. 12a. In some embodiment, the healing cap 1563 is configured to couple with the head section 1565 so as to align the facial-side surface area 1620 with the facial-side surface area 1520. In some embodiment, the healing cap 1563 is configured to couple with the head section 1565 so as to align the interproximal-side surface area 1615 with the interproximal-side surface area 1515. In some embodiment, the healing cap 1563 is configured to couple with the head section 1565 so as to align the lingual-side surface area 1625 with the lingual-side surface area 1525. In some embodiment, the healing cap 1563 is configured to couple with the head section 1565 so as to align the interproximal-side surface area 1630 with the interproximal-side surface area 1530.

In some embodiments, the facial-side surface area 1620 and/or the lingual-side surface area 1625 provide an area for bone growth therein to compensate for jawbone deterioration adjacent to the healing cap 1563 due to craniofacial growth. In some embodiments, the facial-side surface area 1620 and/or the narrower lingual-side surface area 1625 provide an arch shaped area for bone growth therein to compensate for jawbone deterioration adjacent to the healing cap 1563 due to craniofacial growth. In some embodiments, the facial-side surface area 1620 and/or the narrower lingual-side surface area 1625 provide a flat area for bone growth to compensate for jawbone deterioration adjacent to the healing cap 1563 due to craniofacial growth. In some embodiments, the facial-side surface area 1620 and/or the narrower lingual-side surface area 1625 provide a concave shaped area for bone growth therein to compensate for jawbone deterioration adjacent to the healing cap 1563 due to craniofacial growth. Increasing bone volume and/or soft tissue volume adjacent to the facial-side surface area 1620 and/or the narrower lingual-side surface area 1625 prevents early exposure of the healing cap 1563.

In some embodiments, the facial-side surface area 1620 and/or the lingual-side surface area 1625 provide a concave shaped area to improve bone formation due to the gap between the existing bone and the facial-side surface area 1620 and/or the lingual-side surface area 1625. In some embodiments, the facial-side surface area 1620 and/or the lingual-side surface area 1625 provide a concave shaped area to allow greater bone growth therein. In some embodiments, the facial-side surface area 1620 and/or the lingual-side surface area 1625 provide a concave shaped area to prevent/minimize pressure between the bone and the healing cap 1563 during and/or immediately after the procedure. Preventing and/or minimizing pressure between the bone and the healing cap 1563 during and/or immediately after the procedure prevent resorption of the bone around the healing cap 1563 and/or allows increased bone formation around the healing cap 1563. In some embodiments, the facial-side surface area 1620 and/or the lingual-side surface area 1625 provide a concave shaped area to allow bone and/or soft tissue growth therein.

While several illustrative embodiments of the invention have been shown and described, numerous variations and alternative embodiments will occur to those skilled in the art. Such variations and alternative embodiments are contemplated, and can be made without departing from the scope of the invention as defined in the appended claims.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The foregoing detailed description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied there from. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . ."

What is claimed is:

1. An implant fixture adapted for implanting into an alveolus of a jawbone of a patient, the jawbone including a facial side and a lingual side, the implant fixture comprising:
  a. a head section integrally formed with a shaft section to form a one piece implant fixture, the head section including a bevel integrally formed with a body of the head section, (i) the bevel including a first exterior concave sidewall facing the facial side and extending to and aligned with a first exterior concave sidewall of the body also facing the facial side which in turn extends to and is aligned with a tapering first upper exterior concave portion of a shaft facing the facial side, the tapering first exterior upper concave portion having a largest surface adjacent a bottom of the first exterior concave sidewall of the body and tapering to a point at a distal end of the first upper exterior portion of the shaft, (ii) the bevel including a first interior concave sidewall aligned with the first exterior concave sidewall of the bevel and terminating at an interior bottom wall within the bevel, (iii) the bevel including a second exterior concave sidewall facing the lingual side and extending to and aligned with a second exterior concave sidewall of the body also facing the lingual side which in turn extends to and is aligned with a second upper exterior portion of a shaft facing the lingual side, (iv) the bevel including a second interior concave sidewall aligned with the second exterior concave sidewall of the bevel and terminating at an interior bottom wall within the bevel, (v) the bevel including a first convex interproximal exterior sidewall between the first exterior concave sidewall and the second exterior concave sidewall and extends to and is aligned with a first convex interproximal sidewall of the body which in turn extends to a first upper convex interproximal portion of the shaft, (vi) the bevel including a first convex interproximal interior sidewall aligned with the first convex interproximal exterior sidewall of the bevel and terminating at an interior bottom wall within the bevel, (vii) the bevel including an oppositely disposed second convex interproximal exterior sidewall between the first exterior concave sidewall and the second exterior concave sidewall and extends to and is aligned with a second convex interproximal sidewall of the body which in turn extends to a second upper convex interproximal portion of the shaft, (viii) the bevel including a second convex interproximal interior sidewall aligned with the second convex interproximal exterior sidewall of the bevel and terminating at an interior bottom wall within the bevel;

(ix) the bevel including an interior chamber open at its top, bounded by said first interior concave sidewall, said second interior concave sidewall, said first interior convex sidewall, said second interior convex sidewall, and an interior surface of an interior bottom wall, (x) the first exterior concave sidewall of the bevel deeper into the interior chamber of the bevel than the second exterior concave sidewall of the bevel and the first exterior concave sidewall of the body deeper into the body than the second exterior concave sidewall of the body;

b. the shaft including a first lower portion facing the facial side and extending from the distal end of the first upper portion of the shaft facing the facial side to a bottom surface at a distal end of the shaft, the shaft including at least a second portion facing the lingual side and extending from adjacent a bottom of the body of the head section to said bottom surface at said distal end of the shaft, a first convex interproximal portion between the first upper portion and first lower portion of the shaft facing the facial side and said at least said second portion of the shaft facing the lingual side, and an oppositely disposed second convex interproximal portion between the first upper portion and first lower portion of the shaft facing the facial side and said at least said second portion of the shaft facing the lingual side, the first convex interproximal portion extending from adjacent a bottom of the body of the head section to said bottom surface at said distal end of the shaft, the second convex interproximal portion extending from adjacent a bottom of the body of the head section to said bottom surface at said distal end of the shaft;

c. said shaft downwardly tapered from adjacent the bottom of the body of the head section to its distal end, the shaft having outer surfaces with screw threads extending over an outer surface of the first convex interproximal portion and over an outer surface of the second convex interproximal portion but not extending over said first upper exterior concave portion of the shaft facing the facial side and a corresponding portion of the second portion of the shaft facing the lingual side, the screw threads continuously extending over aligned outer surfaces of the first convex interproximal portion, said first lower exterior concave portion of the shaft facing the facial side and a corresponding portion of the second portion of the shaft facing the lingual side, and the second convex interproximal portion to adjacent said bottom surface;

d. wherein, the first exterior concave portion of the bevel, the first exterior concave portion of the body of the head section and the tapering first upper exterior concave portion of the shaft accommodate a contour of gingival tissue at the facial side of a patient's oral cavity and provides an area for bone growth to compensate for jawbone deterioration adjacent to the implant fixture due to cranialfacial growth, the second exterior concave portion of the bevel and the second exterior concave portion of the body of the head section accommodate a contour of gingival tissue at the lingual side of a patient's oral cavity and provides an area for bone growth to compensate for jawbone deterioration adjacent to the implant fixture due to cranialfacial growth, the first convex section accommodates gingival tissue at a first interproximal side of a patient's oral cavity, the second convex section accommodates gingival tissue at a second interproximal side of a patient's oral cavity and e. wherein, the outer screw threads on the shaft provide a surface area into which bone growth is formed to prevent the implant fixture from vertical and rotational movement within the jawbone.

2. The implant fixture in accordance with claim 1 further comprising: an interior threaded chamber extending from a central location of the interior surface of said interior bottom wall of said bevel into a portion of said interior bottom wall.

3. The implant fixture in accordance with claim 1 further comprising:

a. the second upper exterior portion of the shaft facing the lingual side is concave and is aligned with the second exterior concave sidewall of the body, the second upper exterior portion of the shaft tapering and having a largest surface adjacent a bottom of the second exterior sidewall of the body and tapering to a point at a distal end of the second upper exterior portion of the shaft; and b. the shaft including a second lower portion facing the lingual side and extending from the distal end of the second upper portion of the shaft facing the lingual side to a bottom surface at a distal end of the shaft.

4. The implant fixture in accordance with claim 1 further comprising: the body of the head section further including microthreads on the first convex interproximal sidewall of the body.

5. The implant fixture in accordance with claim 1 further comprising: the body of the head section further including microthreads on the opposite second interproximal sidewall of the body.

6. An implant fixture adapted for implanting into an alveolus of a jawbone of a patient, the jawbone including a facial side and a lingual side, the implant fixture comprising:
   a. a head section integrally formed with a shaft section to form a one piece implant fixture, the head section including a bevel integrally formed with a body of the head section,
      (i) the bevel including a first exterior concave sidewall facing the facial side and extending to and is aligned with a first exterior concave sidewall of the body also facing the facial side which in turn extends to and is aligned with a tapering first upper exterior concave portion of a shaft facing the facial side, the tapering first exterior upper concave portion having a largest surface adjacent a bottom of the first exterior concave sidewall of the body and tapering to a point at a distal end of the first upper exterior portion of the shaft,
      (ii) the bevel including a second exterior concave sidewall facing the lingual side and extending to and aligned with a second exterior concave sidewall of the body also facing the lingual side which in turn extends to and is aligned with a second upper exterior portion of a shaft facing the lingual side,
      (iii) the bevel including a first convex interproximal exterior sidewall between the first exterior concave sidewall and the second exterior concave sidewall and extends to and is aligned with a first convex interproximal sidewall of the body which in turn extends to an upper convex interproximal portion of the shaft,
      (iv) the bevel including an oppositely disposed second convex interproximal exterior sidewall between the first exterior concave sidewall and the second exterior concave sidewall and extends to and is aligned with a second convex interproximal sidewall of the body which in turn extends to a second upper convex interproximal portion of the shaft,
      (v) the first exterior concave sidewall of the bevel deeper into the bevel than the second exterior concave sidewall of the bevel and the first exterior concave sidewall of the body deeper into the body than the second exterior concave sidewall of the body;
   b. the shaft including a first lower portion facing the facial side and extending from the distal end of the first upper portion of the shaft facing the facial side to a bottom surface at a distal end of the shaft, the shaft including at least a second portion facing the lingual side and extending from adjacent a bottom of the body of the head section to said bottom surface at said distal end of the shaft, a first convex interproximal portion between the first upper portion and first lower portion of the shaft facing the facial side and said at least said second portion of the shaft facing the lingual side, and an oppositely disposed second convex interproximal portion between the first upper portion and first lower portion of the shaft facing the facial side and said at least said second portion of the shaft facing the lingual side, the first convex interproximal portion extending from adjacent a bottom of the body of the head section to said bottom surface at said distal end of the shaft, the second convex interproximal portion extending from adjacent a bottom of the body of the head section to said bottom surface at said distal end of the shaft;
   c. said shaft downwardly tapered from adjacent the bottom of the body of the head section to its distal end, the shaft having outer surfaces with screw threads extending over an outer surface of the first convex interproximal portion and over an outer surface of the second convex interproximal portion but not extending over said first upper exterior concave portion of the shaft facing the facial side and a corresponding portion of the second portion of the shaft facing the lingual side, the screw threads continuously extending over aligned outer surfaces of the first convex interproximal portion, said first lower exterior portion of the shaft facing the facial side and a corresponding portion of the second portion of the shaft facing the lingual side, and the second convex interproximal portion to adjacent said bottom surface;
   d. wherein, the first exterior concave portion of the bevel, the first exterior concave portion of the body of the head section and the tapering first upper exterior concave portion of the shaft accommodate a contour of gingival tissue at the facial side of a patient's oral cavity and provides an area for bone growth to compensate for jawbone deterioration adjacent to the implant fixture due to cranialfacial growth, the second exterior concave portion of the bevel and the second exterior concave portion of the body of the head section accommodate a contour of gingival tissue at the lingual side of a patient's oral cavity and provides an area for bone growth to compensate for jawbone deterioration adjacent to the implant fixture due to cranialfacial growth, the first convex section accommodates gingival tissue at a first interproximal side of a patient's oral cavity, the second convex section accommodates gingival tissue at a second interproximal side of a patient's oral cavity; and
   e. wherein, the outer screw threads on the shaft provide a surface area into which bone growth is formed to prevent the implant fixture from vertical and rotational movement within the jawbone.

7. The implant fixture in accordance with claim 6 further comprising:
   a. the second upper exterior portion of the shaft facing the lingual side is concave and is aligned with the second exterior concave sidewall of the body, the second upper exterior portion of the shaft tapering and having a largest surface adjacent a bottom of the second exterior sidewall of the body and tapering to a point at a distal end of the second upper exterior portion of the shaft; and
   b. the shaft including a second lower portion facing the lingual side and extending from the distal end of the second upper portion of the shaft facing the lingual side to a bottom surface at a distal end of the shaft.

8. The implant fixture in accordance with claim 6 further comprising: the body of the head section further including microthreads on the first convex interproximal sidewall of the body.

9. The implant fixture in accordance with claim 6 further comprising: the body of the head section further including microthreads on the opposite second interproximal sidewall of the body.

10. An implant fixture adapted for implanting into an alveolus of a jawbone of a patient, the jawbone including a facial side and a lingual side, the implant fixture comprising:
   a. a head section integrally formed with a shaft section to form a one piece implant fixture, the head section including a body of the head section,
      (i) the body having a first exterior concave sidewall facing the facial side which in turn extends to and is aligned with a tapering first upper exterior concave portion of a shaft facing the facial side, the tapering first exterior upper concave portion having a largest surface adjacent a bottom of the first exterior concave sidewall of the body and tapering to a point at a distal end of the first upper exterior portion of the shaft,
      (ii) the body including a second exterior concave sidewall facing the lingual side which in turn extends to and is aligned with a second upper exterior portions of a shaft facing the lingual side,
      (iii) the body including a first convex interproximal exterior sidewall between the first exterior concave sidewall and the second exterior concave sidewall and extends to and is aligned with an upper convex interproximal portion of the shaft,
      (iv) the body including an oppositely disposed second convex interproximal exterior sidewall between the first exterior concave sidewall and the second exterior concave sidewall and extends to and is aligned with a second upper convex interproximal portion of the shaft,
      (v) the first exterior concave sidewall of the body deeper into the body than the second exterior concave sidewall of the body;
   b. the shaft including a first lower portion facing the facial side and extending from the distal end of the first upper portion of the shaft facing the facial side to a bottom surface at a distal end of the shaft, the shaft including at least a second portion facing the lingual side and extending from adjacent a bottom of the body of the head section to said bottom surface at said distal end of the shaft, a first convex interproximal portion between the first upper portion and first lower portion of the shaft facing the facial side and said at least said second portion of the shaft facing the lingual side, and an oppositely disposed second convex interproximal portion between the first upper portion and first lower portion of the shaft facing the facial side and said at least said second portion of the shaft facing the lingual side, the first convex interproximal portion extending from adjacent a bottom of the body of the head section to said bottom surface at said distal end of the shaft, the second convex interproximal portion extending from adjacent a bottom of the body of the head section to said bottom surface at said distal end of the shaft;
   c. said shaft downwardly tapered from adjacent the bottom of the body of the head section to its distal end, the shaft having outer surfaces with screw threads extending over an outer surface of the first convex interproximal portion and over an outer surface of the second convex interproximal portion but not extending over said first upper exterior concave portion of the shaft facing the facial side and a corresponding portion of the second portion of the shaft facing the lingual side, the screw threads continuously extending over aligned outer surfaces of the first convex interproximal portion, said first lower exterior portion of the shaft facing the facial side and a corresponding portion of the second portion of the shaft facing the lingual side, and the second convex interproximal portion to adjacent said bottom surface;
   d. wherein, the first exterior concave portion of the body of the head section and the tapering first upper exterior concave portion of the shaft accommodate a contour of gingival tissue at the facial side of a patient's oral cavity and provides an area for bone growth to compensate for jawbone deterioration adjacent to the implant fixture due to cranialfacial growth, the second exterior concave portion of the body of the head section accommodate a contour of gingival tissue at the lingual side of a patient's oral cavity and provides an area for bone growth to compensate for jawbone deterioration adjacent to the implant fixture due to cranialfacial growth, the first convex section accommodates gingival tissue at a first interproximal side of a patient's oral cavity, the second convex section accommodates gingival tissue at a second interproximal side of a patient's oral cavity; and
   e. wherein, the outer screw threads on the shaft provide a surface area into which bone growth is formed to prevent the implant fixture from vertical and rotational movement within the jawbone.

11. The implant fixture in accordance with claim 10 further comprising:
   a. the second upper exterior portion of the shaft facing the lingual side is concave and is aligned with the second exterior concave sidewall of the body, the second upper exterior portion of the shaft tapering and having a largest surface adjacent a bottom of the second exterior sidewall of the body and tapering to a point at a distal end of the second upper exterior portion of the shaft; and
   the shaft including a second lower portion facing the lingual side and extending from the distal end of the second upper portion of the shaft facing the lingual side to a bottom surface at a distal end of the shaft.

12. The implant fixture in accordance with claim 10 further comprising: the body of the head section further including microthreads on the first convex interproximal sidewall of the body.

13. The implant fixture in accordance with claim 10 further comprising: the body of the head section further including microthreads on the opposite second interproximal sidewall of the body.

14. An implant fixture adapted for implanting into an alveolus of a jawbone of a patient, the jawbone including a facial side and a lingual side, the implant fixture comprising:
   a. a head section integrally formed with a shaft section to form a one piece implant fixture, the head section including a bevel integrally formed with a body of the head section,
      (i) the bevel including an upper surface of an interior bevel-body having a first exterior concave sidewall facing the facial side and extending to and is aligned with a first exterior concave sidewall of the body also facing the facial side which in turn extends to and is aligned with a tapering first upper exterior concave portion of a shaft facing the facial side, the tapering first exterior upper concave portion having a largest surface adjacent a bottom of the first exterior concave sidewall of the body and tapering to a point at a distal end of the first upper exterior portion of the shaft, (ii) the bevel including a second exterior concave sidewall facing the lingual side and extending to and aligned with a second exterior concave sidewall of the body also facing the lingual side which in turn extends to and is aligned with a second upper exterior portions of a shaft facing the lingual side, (iii) the bevel including a first convex interproximal exterior sidewall between the first exterior concave sidewall and the second exterior concave sidewall and extends to and is aligned with a first convex interproximal sidewall of the body which in turn extends to an upper convex interproximal portion of the shaft, (iv) the bevel including an oppositely disposed second convex interproximal exterior sidewall between the first exterior concave sidewall and the second exterior concave sidewall and extends to and is aligned with a second convex interproximal sidewall of the body which in turn extends to a second upper convex interproximal portion of the shaft, (v) the bevel including an upper surface extending between the first exterior concave sidewall and the second exterior concave sidewall and between the first convex interproximal exterior sidewall and the oppositely disposed second convex exterior interproximal sidewall, the upper surface of the bevel including a central opening in the upper surface leading to an interior threaded bore extending at least partially into the bevel body, a first aperture in said top surface of said bevel adjacent said central opening and an oppositely disposed second aperture in said top surface of said bevel adjacent said central opening, (vi) the first exterior concave sidewall of the bevel deeper into the bevel body than the second exterior concave sidewall of the bevel and the first exterior concave sidewall of the body deeper into the body than the second exterior concave sidewall of the body;

b. the shaft including a first lower portion facing the facial side and extending from the distal end of the first upper portion of the shaft facing the facial side to a bottom surface at a distal end of the shaft, the shaft including at least a second portion facing the lingual side and extending from adjacent a bottom of the body of the head section to said bottom surface at said distal end of the shaft, a first convex interproximal portion between the first upper portion and first lower portion of the shaft facing the facial side and said at least said second portion of the shaft facing the lingual side, and an oppositely disposed second convex interproximal portion between the first upper portion and first lower portion of the shaft facing the facial side and said at least said second portion of the shaft facing the lingual side, the first convex interproximal portion extending from adjacent a bottom of the body of the head section to said bottom surface at said distal end of the shaft, the second convex interproximal portion extending from adjacent a bottom of the body of the head section to said bottom surface at said distal end of the shaft;

c. said shaft downwardly tapered from adjacent the bottom of the body of the head section to its distal end, the shaft having outer surfaces with screw threads extending over an outer surface of the first convex interproximal portion and over an outer surface of the second convex interproximal portion but not extending over said first upper exterior concave portion of the shaft facing the facial side and a corresponding portion of the second portion of the shaft facing the lingual side, the screw threads continuously extending over aligned outer surfaces of the first convex interproximal portion, said first lower exterior portion of the shaft facing the facial side and a corresponding portion of the second portion of the shaft facing the lingual side, and the second convex interproximal portion to adjacent said bottom surface;

d. wherein, the first exterior concave portion of the bevel, the first exterior concave portion of the body of the head section and the tapering first upper exterior concave portion of the shaft accommodate a contour of gingival tissue at the facial side of a patient's oral cavity and provides an area for bone growth to compensate for jawbone deterioration adjacent to the implant fixture due to cranialfacial growth, the second exterior concave portion of the bevel and the second exterior concave portion of the body of the head section accommodate a contour of gingival tissue at the lingual side of a patient's oral cavity and provides an area for bone growth to compensate for jawbone deterioration adjacent to the implant fixture due to cranialfacial growth, the first convex section accommodates gingival tissue at a first interproximal side of a patient's oral cavity, the second convex section accommodates gingival tissue at a second interproximal side of a patient's oral cavity and e. wherein, the outer screw threads on the shaft provide a surface area into which bone growth is formed to prevent the implant fixture from vertical and rotational movement within the jawbone.

15. The implant fixture in accordance with claim 14 further comprising: the bevel including a second exterior concave sidewall facing the lingual side and extending to and aligned with a second exterior concave sidewall of the body also facing a lingual side which in turn extends to and is aligned with a tapering first upper concave portion of the shaft facing the lingual side, the tapering first exterior upper concave portion having a larger surface adjacent a bottom of the first exterior concave sidewall of the body and tapering to a point at a distal end of the first upper exterior portion of the shaft.

16. The implant fixture in accordance with claim 14 further comprising: the body of the head section further including microthreads on the first convex interproximal sidewall of the body.

17. The implant fixture in accordance with claim 14 further comprising: the body of the head section further including microthreads on the opposite second interproximal sidewall of the body.

* * * * *